(12) United States Patent
Nilsson et al.

(10) Patent No.: US 7,867,718 B2
(45) Date of Patent: Jan. 11, 2011

(54) METHODS FOR DETERMINING CONFORMATIONAL CHANGES AND SELF-ASSEMBLY OF PROTEINS

(75) Inventors: Peter Nilsson, Linkoping (SE); Anna Herland, Linkoping (SE); Per Hammarstrom, Linkoping (SE); Peter Asberg, Linkoping (SE); Olle Inganas, Linkoping (SE)

(73) Assignee: BioChromix AB, Linkoping (SE)

( * ) Notice: Subject to any disclaimer, the term of this patent is extended or adjusted under 35 U.S.C. 154(b) by 578 days.

(21) Appl. No.: 11/579,741

(22) PCT Filed: Feb. 22, 2005

(86) PCT No.: PCT/SE2005/000248
§ 371 (c)(1),
(2), (4) Date: Feb. 7, 2007

(87) PCT Pub. No.: WO2005/109005
PCT Pub. Date: Nov. 17, 2005

(65) Prior Publication Data
US 2008/0038751 A1 Feb. 14, 2008

(30) Foreign Application Priority Data
May 10, 2004 (SE) .................................. 0401219

(51) Int. Cl.
*G01N 33/53* (2006.01)
(52) U.S. Cl. ........................................... 435/7.1
(58) Field of Classification Search .................... None
See application file for complete search history.

(56) References Cited

U.S. PATENT DOCUMENTS 5,545,531 A * 8/1996 Rava et al. ..................... 506/23
5,985,242 A * 11/1999 Findeis et al. ................ 424/9.1
6,743,640 B2 * 6/2004 Whitten et al. ............... 436/518

FOREIGN PATENT DOCUMENTS

| WO | WO 9967423 | * 12/1999 |
| WO | WO 02/081735 | 10/2002 |
| WO | WO 03/096016 | * 11/2003 |

OTHER PUBLICATIONS

Ho et al., "Optical sensors Based on Hybrid Aptamer/Conjugated Polymer Complexes", J. Am. Chem. Soc. 2004, 126, 1384-1387.*
Faid et al., "Responsive Supramolecular Polythiophene Assemblies", J. Am. Chem. Soc. 1998, 120, 5274-5278.*
Nilsson et al., [Self-assembly of synthetic peptides control conformation and optical properties of a zwitterionic polythiophene derivative, PNAS, Sep. 2, 2003, vol. 100, No. 18].*
*Common Core Structure of Amyloid Fibrils by Synchrotron X-ray Diffraction*; Margaret Sunde et al.; pp. 729-739; Journal of Molecular Biology, 1997.
*Optical Emission of a Conjugated Polyelectrolyte: Calcium-Induced Conformational Changes in Calmodulin and Calmodulin-Calcineurin Interactions*; K. Peter R. Nilsson et al., pp. 9109-9113; Macromolecules, American Chemical Society; Oct. 2004.
*Chip and Solution Detection of DNA Hybridization Using a Luminescent Zwitterionic Polythiophene Derivative*; K. Peter R. Nilsson et al.; pp. 419-425; Nature Publishing Group, vol. 2, Jun. 2003.
*Colorimetric and Fluorometric Detection of Nucleic Acids Using Cationic Polythiophene Derivatives*; Hoang-Anh Ho et al.; pp. 1548-1551; Agnew. Chem. Int., 41, 9; 2002.
*Optical Sensors Based on Hybrid Aptamer/Conjuqated Polymer Complexes*; Hoang-Anh Ho et al.; pp. 1384-1387, JACS; Jan. 2004.
*Fluorescent Polymeric Transducer for the Rapid, Simple, and Specific Detection of Nucleic Acids at the Zeptomole Level*; Kim Dore et al.; pp. 4240-4244; JACS; Oct. 2003.
*Polythiophene with a Free Amino Acid Side Chain*; Mats Andersson et al.; pp. 546-548; Polymer Communications, 1991, vol. 32, No. 18.
*Controlling Inter-chain and Intra-chain Excitations of a Poly(thiophene) Derivative in Thin Films*; Magnus Berggren et al.; pp. 84-90; Chemical Physics Letters; Apr. 1999.
*Photovoltaic Cells with a Conjugated Polyelectrolyte*; L. Ding et al.; pp. 133-140; Synthetic Metals; Oct. 1999.
*Conformational Transitions of a Free Amino-Acid-Functionalized Polythiophene Induced by Different Buffer Systems*; K.P.R. Nilsson et al.; pp. 10011-10020; Journal of Physics: Condensed Matter; 2002.
*Self-Assembly of Synthetic Peptides Control Conformation and Optical Properties of a Zwitterionic Polythiophene Derivative*; K.Peter R. Nilsson et al. pp. 10170-10174; PNAS; Dec. 2006.
*From the Cover: Twisting Macromolecular Chains: Self-Assembly of a Chiral Supermolecule from Nonchiral Polythiophene Polyanions and Random-Coil Synthetic Peptides*; K. Peter R. Nilsson et al.; pp. 11197-11202; PNAS; Dec. 2006.

* cited by examiner

*Primary Examiner*—Ann Y Lam
(74) *Attorney, Agent, or Firm*—Foley & Lardner LLP

(57) ABSTRACT

The invention relates to methods for measuring conformational changes and self-assembly/aggregation of proteins, especially the formation of amyloid fibrils, using conjugated polyelectrolytes. The conjugate polyelectrolyte is exposed to the protein whereby the conjugated polyelectrolyte and the protein of interest interact, and a change of a property of the polyelectrolyte in response to conformational changes of the protein is observed. The detected change is used to determine different conformations of the protein, especially the formation of amyloid fibrils.

14 Claims, 19 Drawing Sheets

POWT

PTAA

POMT

PONT f-PONT

METHODS FOR DETERMINING CONFORMATIONAL CHANGES AND SELF-ASSEMBLY OF PROTEINS

FIELD OF THE INVENTION

The present invention relates to methods and devices for detection of conformational changes and self-assembly/aggregation of proteins, especially the formation of amyloid fibrils, using conjugated polyelectrolytes (CPs).

BACKGROUND

The development of materials that are capable of selectively detecting conformational changes in proteins, especially the formation of amyloid fibrils, have received increasing attention, owing to their large potential for being used as analytic tools in clinical chemistry. Amyloid fibrils are normally stained with small molecule dyes, such as Congo red and thioflavin T.

CPs based sensors are sensitive to very minor perturbations, due to amplification by a collective system response and therefore offer a key advantage compared to small-molecule based sensors. The possibility to use CPs as detecting elements for biological molecules requires that polymers are compatible with an aqueous environment. This has been accomplished by making conjugated (and sometimes luminescent) polyelectrolytes, as recently used to detect biomolecules through their impact on the conditions for photoinduced charge or excitation transfer.

CPs have previously been used to detect biospecific interactions, such as receptor/analyte interactions, through the conformational alterations of the polyelectrolyte chains [Nilsson, K. P. R.; Inganäs, O. Nature Materials 2003, 2, 419-424; Ho, H-A. et. al. Angew. Chem. Int. Ed. 2002, 41, 1548; Ho, H-A.; Leclerc, M. J. Am. Chem. Soc. 2004, 126, 1384; Dore, K.; Dubus, S.; Ho, H-A.; Levesque, I.; Brunette, M.; Corbeil, G.; Boissinot, M.; Boivin, G.; Bergeron, M. G.; Boudreau, D.; Leclerc, M. J. Am. Chem. Soc. 2004, 126, 4240; WO02/081735, WO03/096016].

However, the use of CPs as direct probes for the recording of conformational changes and self-assembly/aggregation of proteins, especially the formation of amyloid fibrils, has never been reported.

A need exists for simpler and more sensitive methods for detection of conformational changes and self-assembly/aggregation of proteins, especially the formation of amyloid fibrils. Methods based on CPs that can interact directly with proteins and transduce the conformational alteration of the protein into optical signals, would therefore be desirable.

SUMMARY OF THE INVENTION

Natural biopolymers, such as proteins, frequently have ordered conformations, such as alfa-helix and beta-sheets, which contribute to the three-dimensional ordered structure and the specific function of the biopolymer. Conformational changes of biomolecules are very important in biological systems, as a part of the cell signalling pathways and enzymatic reactions.

Likewise do the conformational alterations of CPs allow direct connection between the geometry of chains and the resulting electronic structure and optical processes. The conformational flexibility of CPs, allows direct correlation between the geometry of chains and the resulting electronic structure and processes. This requires that the CP chain geometry will be governed by the conformational changes of the proteins. If conformational changes of proteins can lead to different conformations of the polyelectrolyte backbone, an alteration of the absorption and emission properties from the polyelectrolyte will be observed. This could therefore be used as a platform for making novel sensors. Methods using fluorescent probes that can record conformational changes and self-assembly/aggregation of proteins are of great interest, as many diseases are associated with structural abnormalities of proteins, such as the formation of amyloid fibrils where alfa-helical structure transforms to beta-sheet rich structure. Examples of such diseases are Alzheimer's disease, Creutzfeldt Jacob disease (CJD), Secondary amyloidosis, type 2 diabetes and bovine spongiform encephalopathy (BSE). As formation of amyloid fibrils is a hallmark of disease and a nuisance during biotechnological protein purification, a simple detection tool of such a process is of great importance.

The objective of the present invention is therefore to provide means and methods that meet these and other needs. This objective is in a first aspect achieved with a method for detecting conformational changes and/or self-assembly/aggregation in a protein using a conjugated polyelectrolyte as a direct probe.

In an at present preferred embodiment, the conformational change or self-assembly/aggregation of proteins is the formation of amyloid fibrils or protofibrils.

Schematically, the method according to the invention comprises the steps:

i) exposing the conjugated polyelectrolyte to the protein;
ii) detecting a change in at least one property of the conjugated polyelectrolyte;
iii) using said change to determine a conformational change or self-assembly/aggregation in said protein.

This method could be further elaborated by a person skilled in the art with additional steps, e.g. measuring a value for the at least one property in which the change should be detected prior to step i).

Preferably the conjugated polyelectrolyte comprises copolymers or homopolymers of thiophene, pyrrole, aniline, furan, phenylene, vinylene, fluorene or their substituted forms, and preferably the conjugated polyelectrolyte has one or more ionic side chain functionalities. The side chain functionalities could be anionic, cationic or zwitterionic and could be selected from the group comprised of amino acids, amino acid derivatives, neurotransmittors, monosaccharides, nucleic acids, and combinations and chemically modified derivatives thereof.

In a preferred embodiment of the invention, the at least one property in which a change should be detected is chosen from the group consisting of fluorescence, Förster Resonance Energy Transfer (FRET), quenching of emitted light, absorption, impedance, refraction index, mass, visco-elastic properties and thickness.

In further embodiments of the invention, either the conjugated polyelectrolyte or the protein in which conformational changes and/or self-assembly/aggregation should be detected is bound, preferably adsorbed or covalently attached, to a solid support, such as a microtiter plate or a flow cell. The conjugated polyelectrolyte and protein could however also be in solution or entrapped in a polymer matrix, or the detection could take place in a tissue sample.

A further aspect of the invention provides the use of a biosensor device for determining conformational changes and self-assembly/aggregation of proteins, comprising a conjugated polyelectrolyte of the kind identified above, and a substrate for said conjugated polyelectrolyte in which said polyelectrolyte is exposable to said target protein and means for detecting a change in the at least one property. The use of the biosensor device is defined in claim 14.

The multiplicity of conformational changes in proteins that one may wish to identify also implies that the invention in a still further aspect can be implemented in the form of a microarray, and which calls for anchoring and patterning of the detecting system on a surface.

DETAILED DESCRIPTION OF THE INVENTION

In general terms, the present invention relates to a novel method for the recording of conformational changes and self-assembly/aggregation of proteins, especially the formation of amyloid fibrils, using conjugated polyelectrolytes. The conjugated polyelectrolyte is exposed to the protein whereby the polyelectrolyte and the protein of interest interact, and a change of a property of said polyelectrolyte in response to conformational changes in said protein is observed. The detected change is used to determine the conformation of said protein.

The invention also relates to a biosensor device comprising such a method for detection of conformational changes and self-assembly/aggregation of proteins, especially the formation of amyloid fibrils.

The invention is based on a conjugated polyelectrolyte interacting directly with said protein. The interaction occurs without covalent bonding and is based on hydrogen bonding, electrostatic- and non-polar interactions between the conjugated polyelectrolyte and the biomolecule, herein referred to as non-covalent bonding, which further includes any type of bonding that is not covalent in nature.

The term "direct probe" as used in this application means a probe that can interact directly with a protein to detect a conformational change, without the need for other macromolecular compounds.

The present invention utilizes that changes in the conformation of the protein, especially the formation of amyloid fibrils, induce conformational transitions of the backbone of the conjugated polyelectrolyte, separation or aggregation of conjugated polyelectrolyte chains. Furthermore, conformational transitions of the backbone of the conjugated polyelectrolyte, separation or aggregation of conjugated polyelectrolyte chains, alter the intra- and inter-chain processes of the conjugated polyelectrolytes. These changes can be detected in solution or on a surface. In particular the present invention allows detection of conformational changes and self-assembly/aggregation of proteins, especially the formation of amyloid fibrils.

The conjugated polyelectrolyte is suitably implemented as an active part of a biosensor device, e.g. by immobilizing the conjugated polyelectrolyte on a substrate in a biosensor cell. Suitably the biosensor device comprises a suitable receptacle for said substrate, and a complex between the conjugated polyelectrolyte and the protein is formed on the substrate.

However, other configurations are possible, e.g. the conjugated polyelectrolyte can be provided in solution and passed through a flow cell while a protein solution is mixed with the flow of complex solution. The interaction can be monitored by various analytical techniques.

The biosensor assembly should have suitable means for detecting the changes in polyelectrolyte properties due to the conformational changes in the protein.

Figure 1:
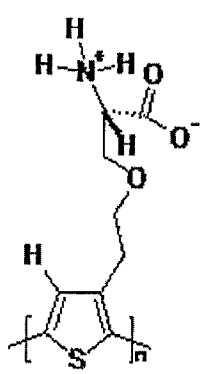
FIG. 1 shows the chemical structure of poly(3-[(S)-5-amino-5-carboxyl-3-oxapentyl]-2,5-thiophenylene hydrochloride) (POWT), a zwitterionic polythiophene derivative, polythiophene acetic acid (PTAA), an anionic polythiophene derivative, poly(3-[(S)-5-amino-5-methoxycarboxyl-3-oxapentyl]-2,5-thiophenylene hydrochloride) (POMT), a cationic polythiophene derivative, poly((3,3"-di[(S)-5-amino-5-carbonyl-3-oxapentyl]-[2,2'; 5',2"])-5,5"-terthiophenylene hydrochloride) (PONT) a zwitterionic polythiophene derivative with a well-defined chain length, and poly((1,4-di(3-[(S)-5 amino-5-carbonyl-3-oxapentyl]-thiophen-2-yl)-benzene)hydrochloride) (f-PONT), a zwittericonic cocopolymer of thiophene and phenylene with a well defined chain length.
Figure 1:
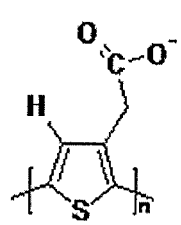
Figure 1:
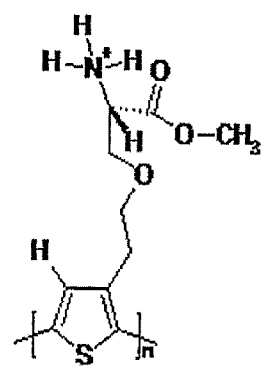
Figure 1:
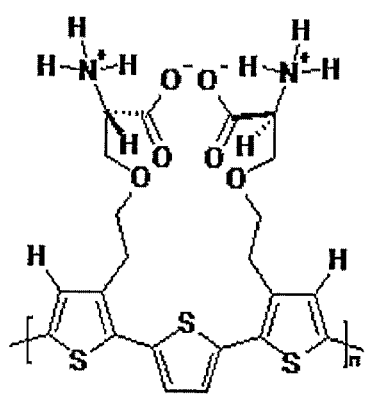
Figure 1:
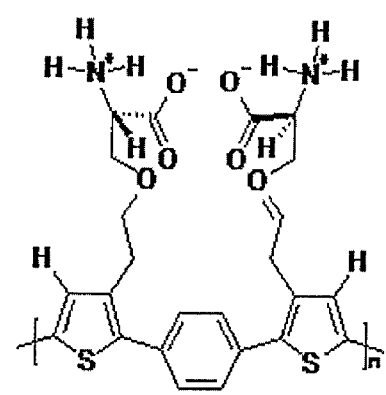
Figure 2:
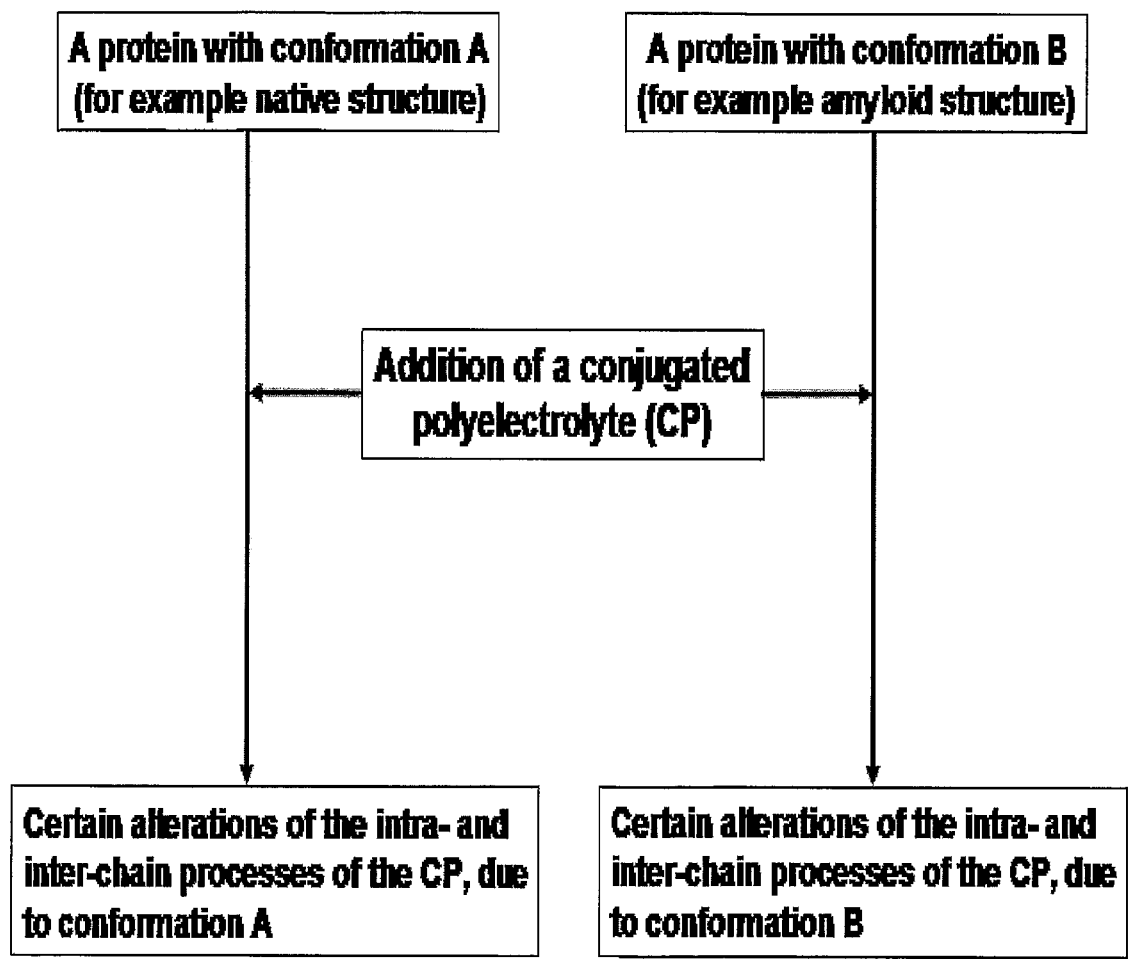
FIG. 2 shows a schematic drawing of the invention.

As examples of conjugated polyelectrolytes exhibiting the above discussed characteristics poly(3-[(S)-5-amino-5-carboxyl-3-oxapentyl]-2,5-thiophenylene hydrochloride) (POWT), polythiophene acetic acid (PTAA), poly (3-[(S)-5-amino-5-methoxycarboxyl-3-oxapentyl]-2,5-thiophenylene hydrochloride) (POMT), poly((3,3"-di[(S)-5-amino-5-carbonyl-3-oxapentyl]-[2,2';5',2"])-5,5"-terthiophenylene hydrochloride) (PONT) and poly((1,4-di(3-[(S)-5 amino-5-carbonyl-3-oxapentyl]-thiophen-2-yl)-benzene) hydrochloride) (f-PONT) (see FIG. 1) can be mentioned. Studies of these polyelectrolytes (see Andersson, M.; Ekeblad, P. O.; Hjertberg, T.; Wennerström, O.; Inganas, O. Polymer Commun. 1991, 32, 546-548; Berggren, M.; Bergman, P.; Fagerström, J.; Inganas, O.; Andersson, M.; Weman, H.; Granström, M.; Stafström, S.; Wennerström, O.; Hjertberg, T. Chem. Phys. Lett. 1999, 304, 84-90; Ding, L.; Jonforsen, M.; Roman, L. S.; Andersson, M. R.; Inganas, 0.2000, Synth. Met., 110, 133-140; Nilsson, K. P. R.; Andersson, M. R.; Inganas, O. Journal of Physics: Condensed Matter 2002, 14, 10011-10020; Nilsson, K. P. R.; Inganäs, O. Nature Materials 2003, 2, 419-424; Nilsson, K. P. R.; Rydberg, J.; Baltzer, L.; Inganäs, O. Proc. Natl. Acad. Sci. USA 2003, 100, 10170-10174. Nilsson, K. P. R.; Rydberg, J.; Baltzer, L.; Inganäs, O. Proc. Natl. Acad. Sci. USA 2004, 101, 11197-11202), have shown interesting optical and electronic processes due to different electrostatic interactions and hydrogen bonding patterns within a single polyelectrolyte chain and between adjacent polyelectrolyte chains. The interactions, due to the ionic side chains, force the polyelectrolyte backbones to adopt alternative conformations, separation or aggregation of polyelectrolyte chains. Especially the separation and aggregation of polyelectrolyte chains induce novel intra- and inter chain processes. The intra-chain processes are related to optical and electronic processes within a polyelectrolyte chain and the inter-chain processes are related to optical and electronic processes between adjacent polyelectrolyte chains. This cause novel optical absorption and emission properties, due to the novel intra- and inter chain processes.

The functional groups of the ionic side chain, charged anionic or cationic at different pH, make these polythiophene derivatives suitable for forming polyelectrolyte complexes with negatively or positively charged oligomers and polymers. In addition, the ionic groups create versatile hydrogen bonding patterns with different molecules.

The detailed description of the invention that follows will deal separately with the conjugated polyelectrolytes, proteins, methods of detection, immobilization of conjugated polyelectrolytes and proteins, and arrays and lines. The invention is finally exemplified with a number of experiments demonstrating the utility thereof.

I Conjugated Polyelectrolytes

The present invention relates to a variety of conjugated polyelectrolytes, with a minimum of 5 mers, consisting of mers derived from the monomers thiophene, pyrrole, aniline, furan, phenylene, vinylene, fluorene or their substituted forms, forming homopolymers and copolymers thereof. The conjugated polyelectrolyte can be mono dispersed, consist of polyelectrolyte chains with a well-defined chain length, or poly dispersed, consist of polyelectrolyte chains with different chain length. Furthermore, monomers with anionic-, cationic or zwitterionic side chain functionalities are included within the scope of the invention. The side chain functionalities are derived from, but not limited to, amino acids, amino acid derivatives, neurotransmittors, monosaccharides, nucleic acids, or combinations and chemically modified derivatives thereof. The conjugated polyelectrolytes of the present invention may contain a single side chain functionality or may comprise two or more different side chain functionalities. The functional groups of the conjugated polyelectrolytes, charged anionic or cationic at different pHs, make these polyelectrolyte derivatives suitable for forming strong polyelectrolyte complexes with negatively or positively charged oligomers and polymers. In addition, the ionic groups create versatile hydrogen bonding patterns with different molecules.

II Proteins

The conjugated polyelectrolytes of the present invention interact with a protein of interest. These interactions are formed without covalent bonding and based on hydrogen bonding, electrostatic- and non-polar interactions between the conjugated polyelectrolytes and the protein. The protein will have the ability to change its conformation and/or self-assemble/aggregate, especially to form amyloid fibrils. The alteration of the protein conformation can occur prior to the complexation of the conjugated polyelectrolyte and the protein, or within the conjugated polyelectrolyte-protein complex. A wide variety of proteins can be used and the choice of protein is only limited by the affinity to the conjugated polyelectrolytes. The proteins can be chemically modified to interact with the conjugated polyelectrolyte of interest. Methods of derivatizing a diverse range of proteins are well known. For example, amino acid side chains can easily be modified to contain polar and non-polar groups, or groups with hydrogen bonding abilities. The protein can be in solution (see example 1-4), or in tissue samples (see example 5-13). The detection of the conformational change or self-assembly/aggregation of the protein can be made in water solutions (see example 1-4), organic solvents, body fluids, or in tissue samples (histological staining, see example 5-13)

III Methods of Detection

As already indicated, the present invention is based on the utilization of alterations of intra- and inter-chain processes of conjugated polyelectrolytes, due to conformational changes of proteins, especially the formation of amyloid fibrils. These alterations can be observed by fluorescence, Förster resonance energy transfer (FRET), quenching of emitted light, absorption, impedance, refraction index, change in mass, visco-elastic properties, change in thickness or other physical properties. The conformational transitions of the backbone of the conjugated polyelectrolyte, separation or aggregation of polyelectrolyte chains will alter the intra- and inter-chain processes of the conjugated polyelectrolyte and can for example be detected as a change in the ratio of the intensities of the emitted light at two or more different wavelengths (see example 2-4). The emission intensities can be recorded by a fluorometer and enhancement of the photon flow in the detector can increase the sensitivity. This can be achieved using a laser as the excitation source.

The fluorometric change can also be detected by the use of a fluorescence microscope or a confocal microscope. A combination of excitation or emission filter can be used and the picture can be recorded by a CCD-camera (see example 5-14), video camera, regular camera or by a Polaroid camera. The pictures can then be analyzed by image processing software on a computer, Image correlation spectroscopy (ICS) or by other means.

Changes in impedance can be detected by using the method of impedance spectroscopy. According to the invention the conjugated polyelectrolytes can be immobilized inside a conducting polymer hydrogel matrix for example [POLY [3,4-(ETHYLENEDIOXY) THIOPHENE]/POLY (STYRENE-SULFONICACID) (PEDOT/PSS).]

Changes in resistance, capacitance and inductance can then be tracked with the conjugated polyelectrolytes, or protein molecules in an aqueous environment.

Surface plasmon resonance (SPR) enables detection of minute changes in refraction index. A change in refraction index occurs when the intra- and inter-chain processes of the conjugated polyelectrolytes are altered due to the conformational changes of the proteins. These alterations can also lead to aggregation of the polyelectrolyte chains and is thus detected as a change in refraction index.

Quartz crystal microbalance and dissipation (QCM-D) is a sensitive and versatile technique to measure both adsorbed mass and visco-elastic properties of adsorbed layers of molecules in liquid. Alteration of the intra- and inter-chain processes of the conjugated polyelectrolyte, due to conformational changes of the proteins, can lead to changes in mass or visco-elastic properties and thus be detected by QCM-D or other techniques. Ellipsometry, imaging or null ellipsometry, is an optical technique that uses polarised light to sense the dielectric properties of a sample and can be used to detect these changes in thickness on a sub-angstrom level. These techniques can thus be used for measuring alteration in intra- and inter chain processes of the conjugated polyelectrolytes.

The detection of conformational changes in proteins using conjugated polyelectrolytes can also be detected by electrical and electrochemical methods. A gel or network of the conjugated polyelectrolyte can be formed, and thus a three dimensional object is obtained where each polymer chain is in (indirect) contact with all chains in the network. If conjugated polyelectrolyte is in a semiconducting state—such as when the luminescence properties is used—it will exhibit a rather low conductivity, which is somewhat difficult to easily distinguish from the ionic conductivity of the aqueous medium surrounding the gel. It is therefore desirable to form highly conducting gels of the sensitive macromolecule that allow electrical conduction in the network. A difficulty is that the doping of the conjugated chains, which gives a metallic polymer and a high conductivity, will not only turn on conductivity but also change the mechanical properties and geometry of the chains, thereby hindering the mechanism at work in the case of luminescence detection. A solution to that problem is the use of two component polymer gels, where one component A gives the high conductivity and another component B the protein interactions. If these two compounds are combined in a suitable manner, the changes of geometry of the gel due to said conformational changes of the proteins can be used to detect conformational changes of the proteins. Component A can be an aqueous dispersion of a highly doped polymer and component B, the conjugated polyelectrolyte can be combined, to make gels. By measuring the DC or AC conductivity of these gels with two point and four point probe methods or by impedance spectroscopy, the change of conductance upon conformational changes in the proteins can be followed.

The intra- and inter-chain processes of the conjugated polyelectrolytes are altered by the conformational changes of the proteins, and leads to changes of the electrochemical properties of the conjugated polyelectrolyte, which can then be used to build electrochemical detectors for conformational changes in proteins. A change of the redox potential of the hydrogel formed in the presence of a protein can be used to detect the conformational changes in the protein.

The above described methods can also be implemented in the form of microarrays, to give an "image" of the composition of a biological sample.

IV Immobilization of Conjugated Polymers and Proteins

The conjugated polyelectrolytes or the proteins can be immobilized on a variety of solid supports, including, but not limited to silicon wafers, glass (e.g. glass slides, glass beads, glass [WAFERS ETC.), SILICON RUBBER, POLYSTYRENE, POLYETHYLENE, TEFLON, SILICA GEL BEADS,] gold, indium tin oxide (ITO coated materials, e.g. glass or plastics), filter paper (e.g. nylon, cellulose and nitrocellulose), standard copy paper or variants and separation media or other chromatographic media. Transfer of the conjugated polyelectrolyte to the solid support can be achieved by using i.a. but not limited to, dip coating, spin-coating, contact printing, screen printing, ink jet technologies, spraying, dispensing and microfluidic printing by the use of soft lithography or the [BIACORE™] (Biacore, Uppsala, Sweden) system.

Immobilization of the conjugated polyelectrolytes is achieved by physical adhesion to the solid support at elevated temperatures or by entrapment in a hydrogel matrix.

Immobilization of the conjugated polyelectrolytes of the present invention may be desired to improve their ease of use, assembly into devices (e.g. arrays or parallel lines), stability, robustness, fluorescent response, to fit into the process of high-throughput-screening (HTS) using micro titer plates and other desired properties.

The proteins of the present invention can be immobilized together with the conjugated polyelectrolyte [(I.] e. mixed with the polyelectrolyte solution). Another way to immobilize the proteins is to place them underneath or on top of the conjugated polyelectrolyte.

Transfer of the protein mixed together with the conjugated polyelectrolyte to the solid support can be achieved by, but not limited to, using dip coating, spin-coating, contact printing, screen printing, ink jet technologies, spraying, dispensing and microfluidic printing by the use of soft lithography (see example 14). If the proteins are to be placed underneath the conjugated polyelectrolyte it has to be transferred to the solid support in the same way as it would have been mixed together with the polyelectrolyte as mentioned above. Placing the proteins on top of the conjugated polyelectrolyte is done in the same way but after the polyelectrolyte has been immobilized to the solid support.

Solvents for the conjugated polyelectrolytes of the present invention and the proteins during the immobilization to the solid support can be, but are not limited to, water, buffered water solutions, methanol, ethanol and combinations thereof. Supporting polymers of other kinds can also be added in this step.

The conjugated polyelectrolyte and the proteins can be entrapped inside polymer matrices on top of a solid support or free floating in solution. A gel or network of the conjugated polyelectrolytes can be formed, where each conjugated polyelectrolyte chain of the present invention is in (indirect) contact with all chains in the network. Realization of these polymer matrices can be done by mixing the conjugated polyelectrolyte with other polymers such as, but not limited to, poly[3,4-(ethylenedioxy) [THIOPHENE]/POLY] (styrenesulfonicacid) (PEDOT/PSS), poly(diallyldimethylammonium chloride) (PDADMAC), poly-4-vinylpyridine (PVPy), poly(pyrrole) (PPy), poly(vinylalcohol) (PVA), poly(aniline) (PANI) or combinations thereof. By swelling these polymer blends in water a hydrogel is realized, which can be of interest when using proteins of biological origin. The conjugated polyelectrolytes of the present invention can be mixed together with these polymers before immobilization to the solid support or transferred afterwards. Proteins of interest can be transferred together with the conjugated polyelectrolyte or in a subsequent step. A microarray or parallel line format can be used if desired, necessary or for other reasons. In certain embodiments of the present invention this network or hydrogel approach can be used to detect conformational changes and aggregation of the conjugated polyelectrolyte chains due to conformational alterations in the protein. These alterations can then be detected by measuring absorption, fluorescence, electrical properties, impedance or by other means.

V Arrays or Lines

According to the present invention the generation of large arrays or parallel lines of the same or different conjugated polyelectrolytes in each spot or line can overcome shortcomings of a single sensor or a solution based approach. The array or parallel line approach opens up the parallel analysis of one or different proteins to one or different-conjugated polyelectrolytes in an easy way. The main purpose of using arrays or lines is to increase ease of use, portability, quantification, selectivity among other qualities and characteristics. With this approach we can explore the ability to measure multi-component samples and to use partially selective sensor spots. This gives the opportunity to analyze two or more samples of interest at the same time, to do on-chip concentration determinations and to study the background. By immobilizing the conjugated polyelectrolyte and/or the proteins on solid supports of any size and in any chosen patterns (such as arrays, lines, spots, posts) small, portable, easily read and interpretable devices can be constructed.

Figure 20:
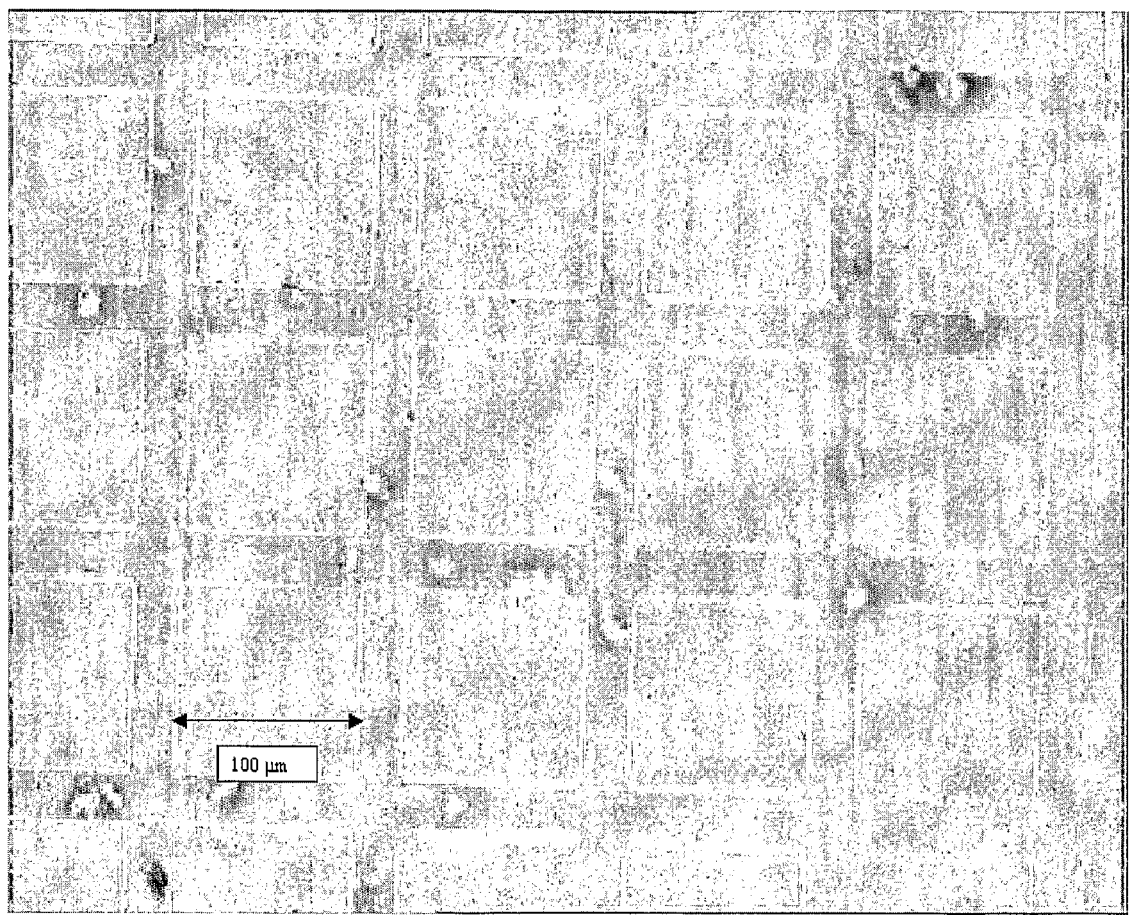
FIG. 20 shows the microcontact printing of POWT. A square net of POWT on plasma etched polystyrene, with lines 25 µm wide surrounding the polystyrene squares of 100×100 µm. Optical microscopy in reflected light.

The use of multiple arrays requires that detection can be done for a great number of proteins, more or less simultaneously. This is often done in the form of a microarray, where many individual detector elements (or probes) are integrated on a small surface area, to allow for massive parallelism in the detection. We have shown that the conjugated polyelectrolyte and the conjugated polyelectrolyte/protein complexes can be printed by micro contact printing using elastomer stamps (FIG. 20). Transfer onto a microarray surface may also be done by spotting conjugated polyelectrolyte solutions, or by ink jetting polyelectrolyte solutions or by the other methods mentioned above. These steps are essential to prepare a multipixel microarray.

EXPERIMENTAL

Example 1

Figure 3:
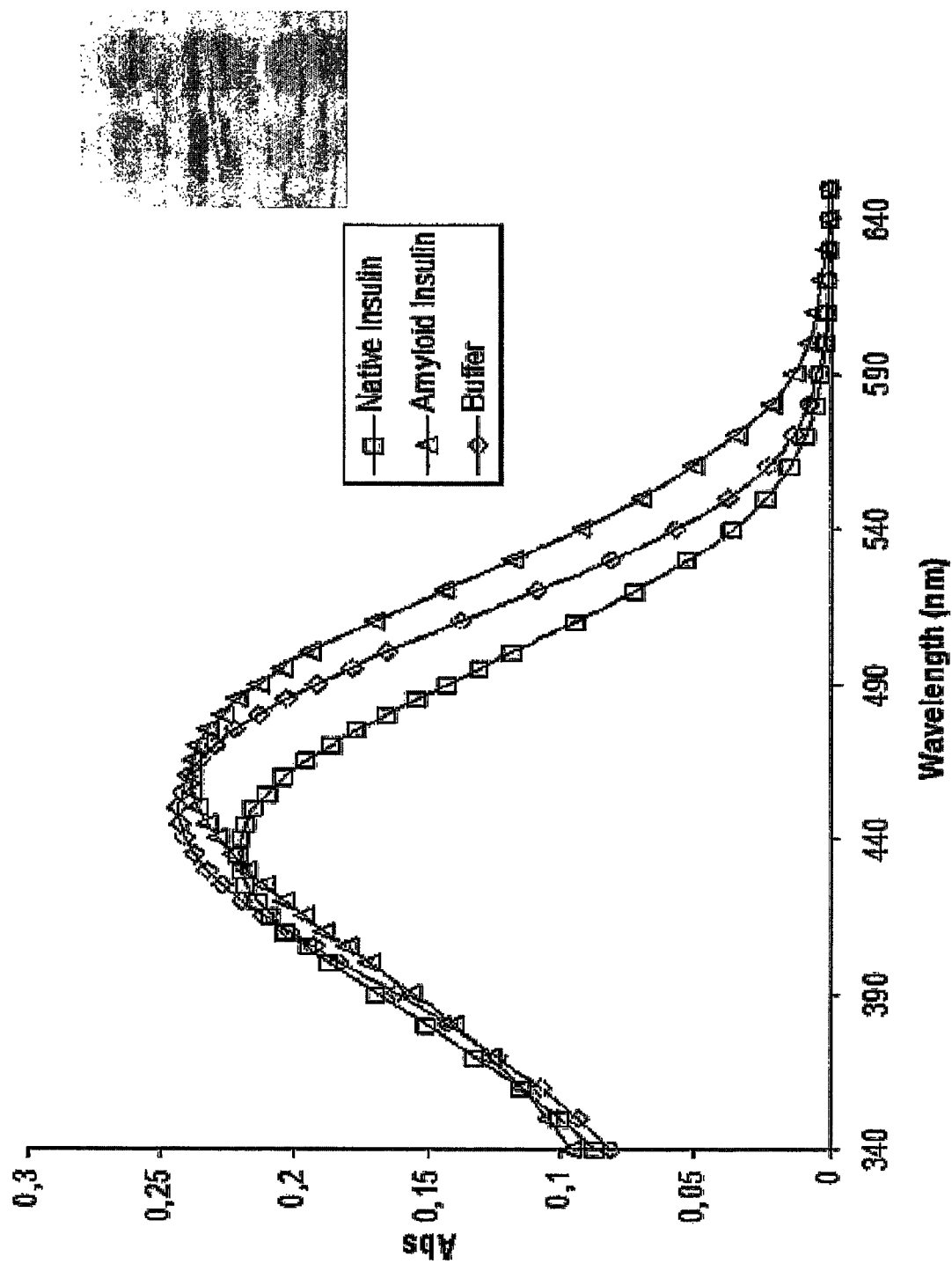
FIG. 3 shows the absorption spectra of 80 µM PTAA (on a monomer basis) with 0 µM insulin, 5 µM native bovine insulin, or 5 µM amyloid bovine insulin, respectively after 5 minutes of incubation in 20 mM Na-phosphate buffer pH 7.0. Insertion showing microtiter plate wells containing PTAA/native bovine insulin (left) and PTAA/amyloid bovine insulin (right).
Figure 4:
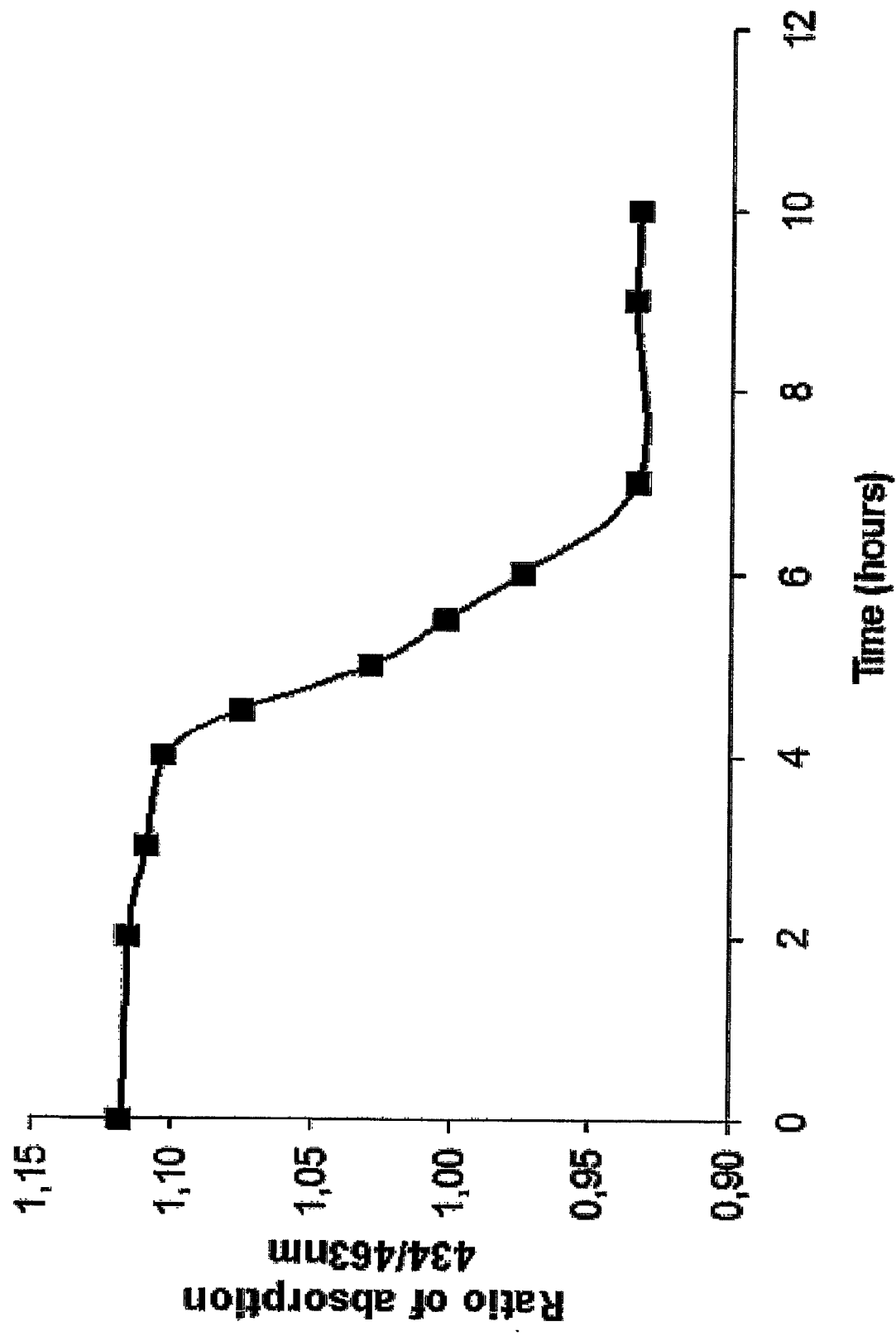
FIG. 4 shows the changes of the intensity of the absorbed light at 434 nm and 463 nm of 80 µM PTAA (on a monomer basis) with an aliquot of 5 µM bovine insulin in 20 mM Na-phosphate buffer pH 7.0, during amyloid formation in the bovine insulin (0.3 mM, pH 1.6 65° C.).

Optical Detection of Amyloid Formation of Bovine Insulin in Solution, Using PTAA A stock-solution containing 1.0 mg PTAA/ml in deionized water was prepared. A stock solution containing 320 µM bovine insulin in 25 mM HCl was placed in a water bath (65° C.) to induce the amyloid formation. For the absorption measurements 10 µl of the polymer stock-solution was mixed with 25 µl of the insulin stock-solution, and diluted to a final volume of 1500 µl with 20 mM Na-phosphate pH 7.0. After 5 minutes of incubation, the absorption spectrum was recorded. Absorption spectra (FIG. 3) were recorded on a Perkin-Elmer Lambda 9 UV/VIS/NIR spectrophotometer for UV/VIS and samples were analyzed during a time period of 2 days.

Example 2

Figure 5:
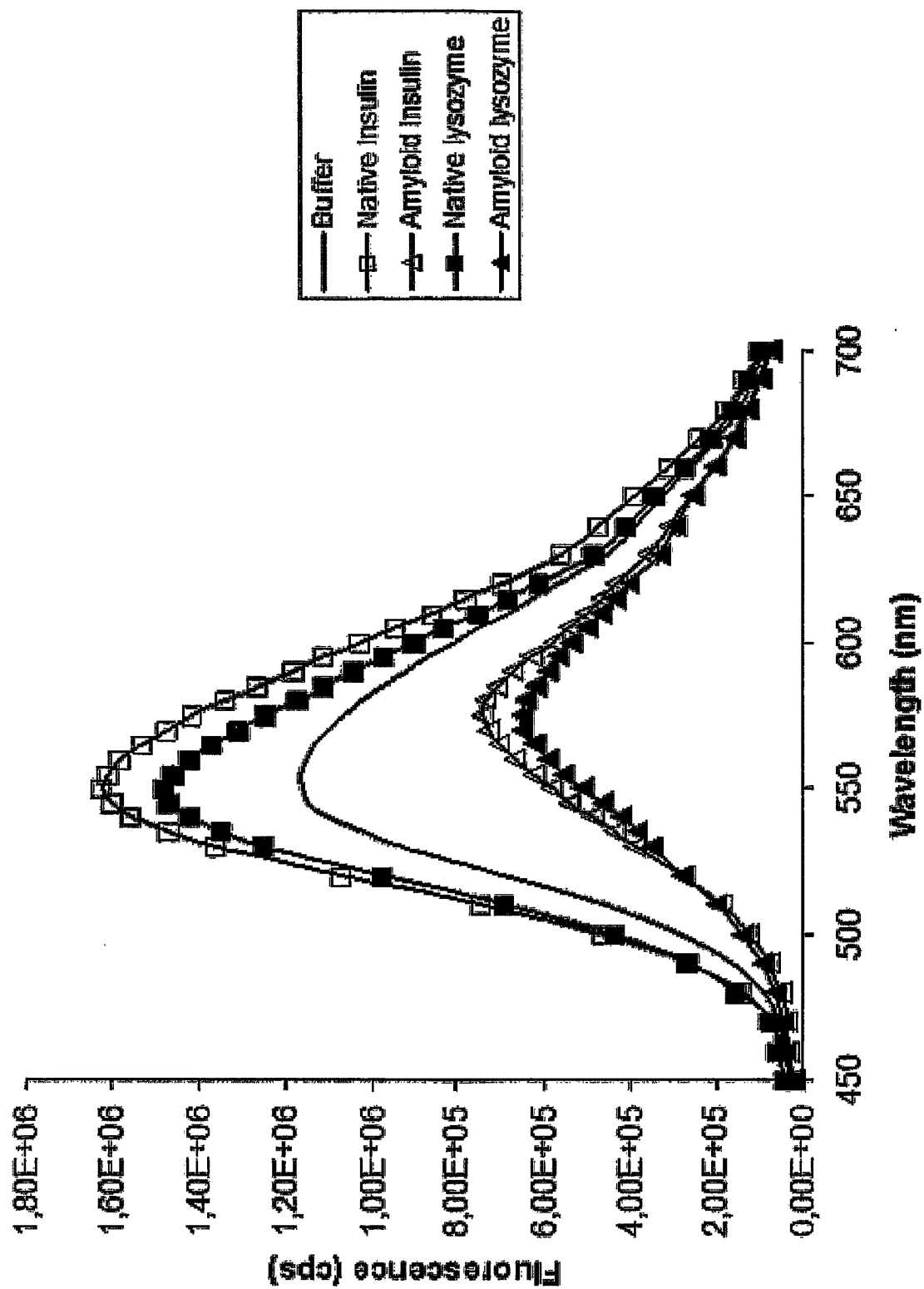
FIG. 5 shows the emission spectra of 80 µM PTAA (on a monomer basis) with 0 µM protein, 5 µM native bovine insulin, 5 µM amyloid bovine insulin, 5 µM native chicken lysozyme, or 5 µM amyloid chicken lysozyme, respectively after 5 minutes of incubation in 20 mM Na-phosphate buffer pH 7.0. All of the emission spectra were recorded with excitation at 400 nm.
Figure 6:
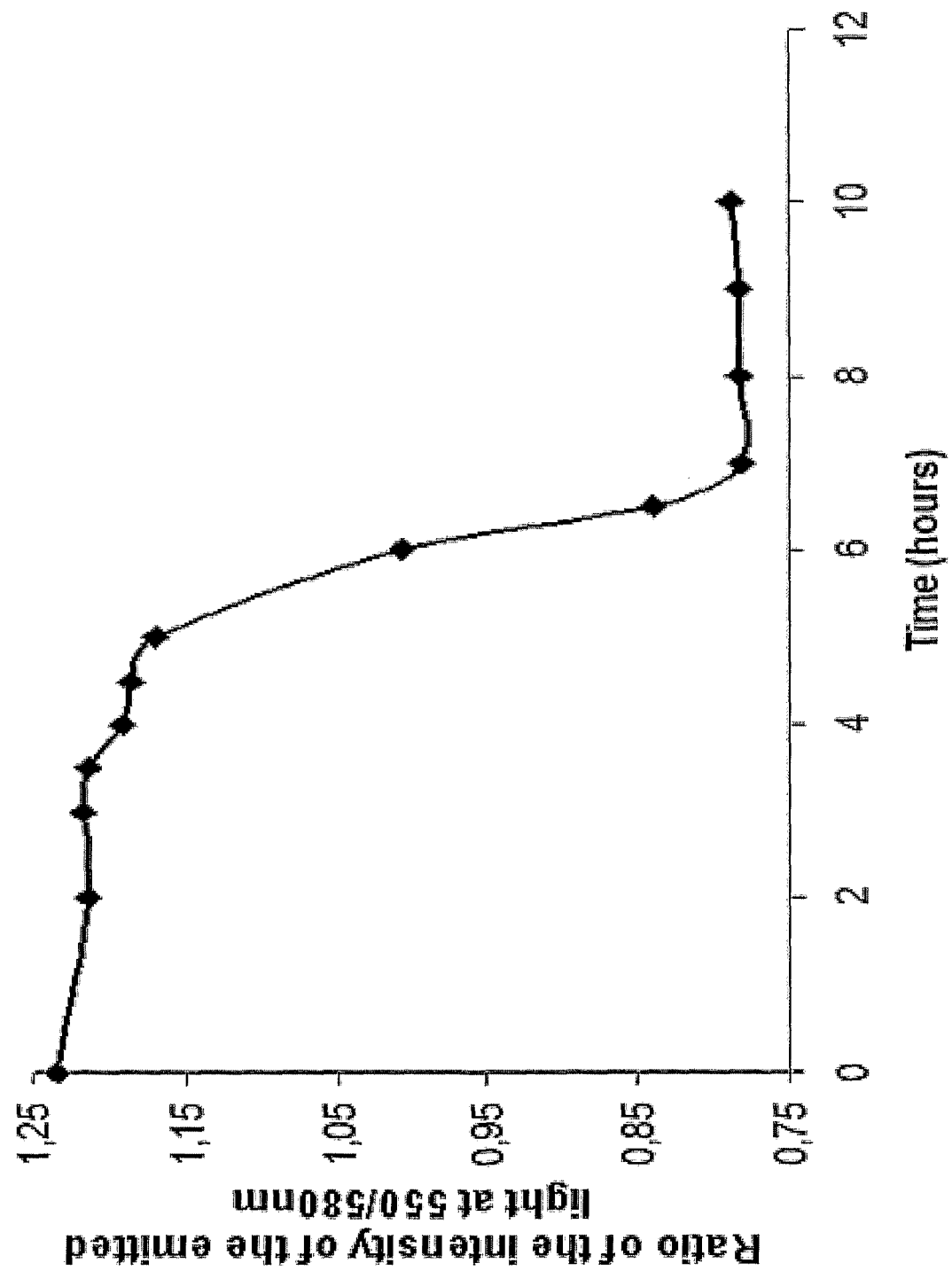
FIG. 6 shows the changes of the ratio of the intensity of the emitted light at 550 nm and 580 nm of 80 µM PTAA (on a monomer basis) with an aliquot of 5 µM insulin in 20 mM Na-phosphate buffer pH 7.0, during amyloid formation in the bovine insulin (0.3 mM, pH 1.6 65° C.).

Fluorescent Detection of Amyloid Formation in Bovine Insulin in Solution, Using PTAA A stock-solution containing 1.0 mg PTAA/ml in deionized water was prepared. A stock solution containing 320 µM bovine insulin in 25 mM HCl was placed in a water bath (65° C.) to induce the amyloid formation. For the emission measurements 10 µl of the polymer stock-solution was mixed with 25 µl of the insulin stock-solution, and diluted to a final volume of 1500 µl with 20 mM Na-phosphate pH 7.0. After 5 minutes of incubation, the emission spectrum was recorded. Emission spectra were recorded on a ISA Jobin-Yvon spex FluoroMax-2 apparatus and samples were analyzed during a time period of 10 hours. All of the spectra were recorded with excitation at 400 nm. Amyloid formation is detected by a decrease of the emitted light and a shift of the emission maximum to a longer wavelength (FIG. 5). The ratio of the intensity of the emitted light at 550 nm and 580 nm can be used to detect amyloid formation of bovine insulin (FIG. 6).

Example 3

Figure 7:
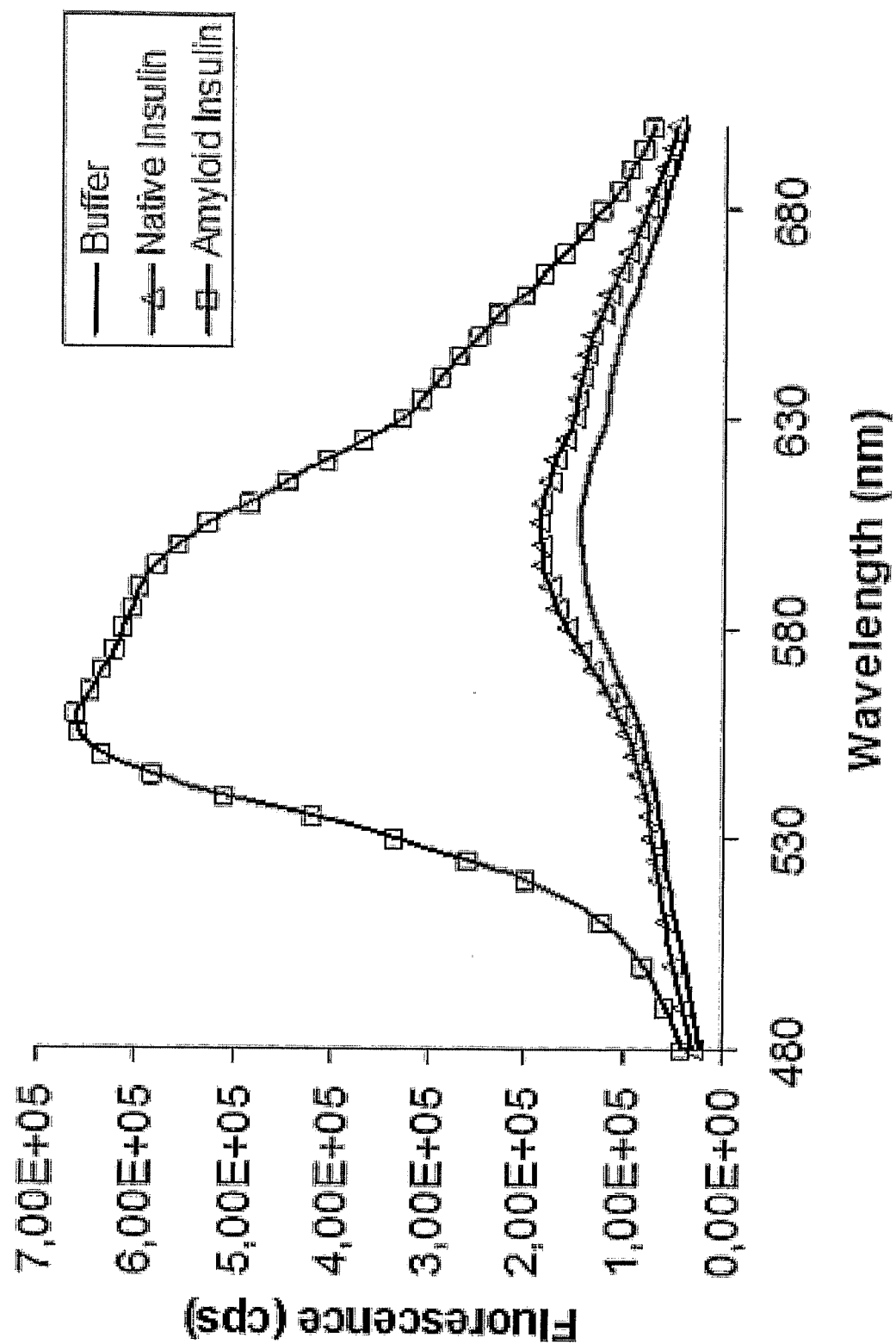
FIG. 7 shows the emission spectra of 6.2 µM PONT with 0 µM insulin, 5 µM native bovine insulin, or 5 µM amyloid bovine insulin, respectively after 5 minutes of incubation in 20 mM Na-phosphate buffer pH 7.0. All of the emission spectra were recorded with excitation at 400 nm.
Figure 8:
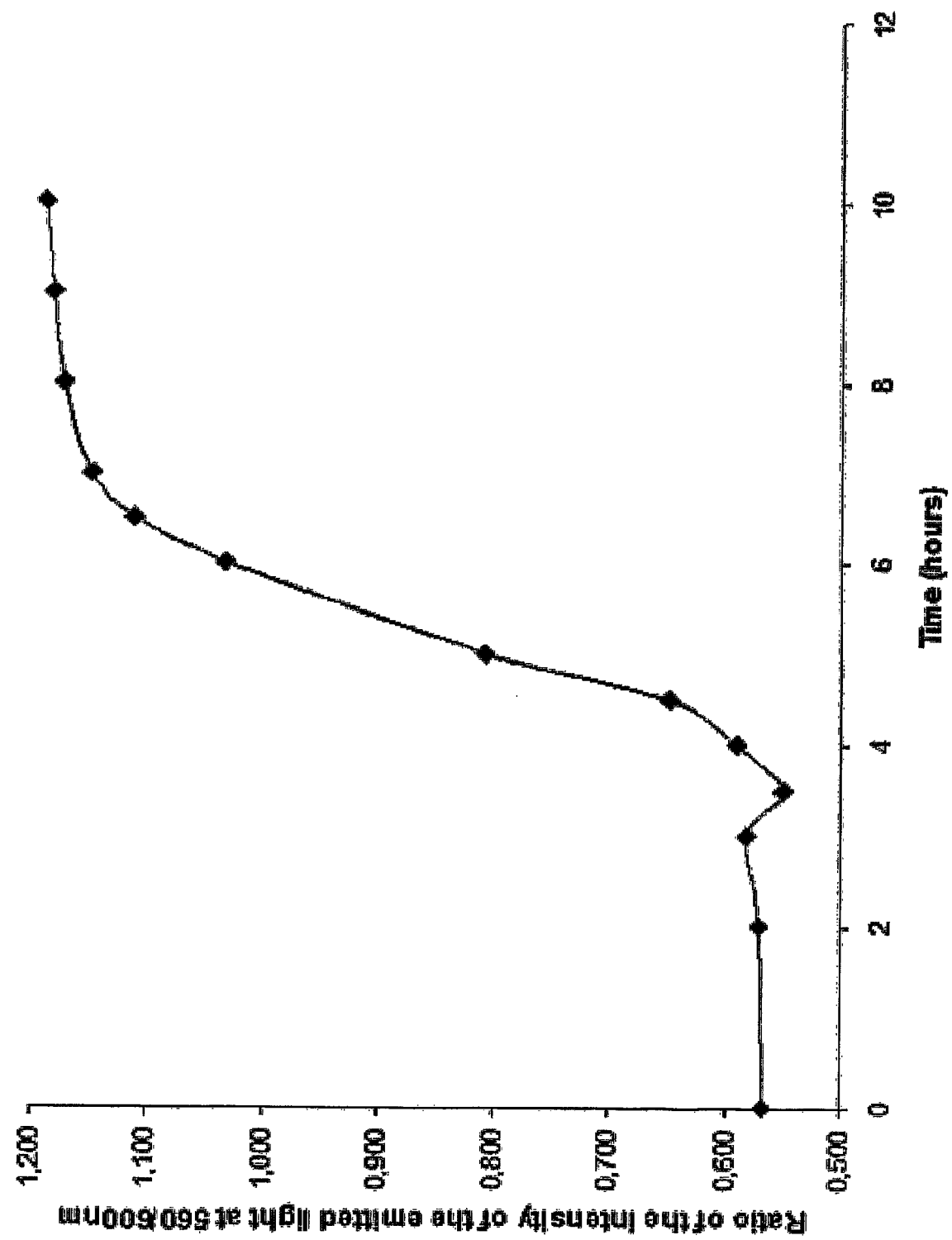
FIG. 8 shows the changes of the ratio of the intensity of the emitted light at 560 nm and 600 nm of 6.2 µM PONT with an aliquot of 5 µM insulin in 20 mM Na-phosphate buffer pH 1.6, during amyloid formation in the bovine insulin (0.3 mM, pH 1.6 65° C.).

Fluorescent Detection of Amyloid Formation of Bovine Insulin in Solution, Using PONT A stock-solution containing 1.5 mg PONT/ml in deionized water was prepared. A stock solution containing 320 µM bovine insulin in 25 mM HCl was placed in a water bath (65° C.) to induce the amyloid formation. For the emission measurements 10 µl of the polymer stock-solution was mixed with 25 µl of the insulin stock-solution, and diluted to a final volume of 1500 µl with 25 mM HCl. After 5 minutes of incubation, the emission spectrum was recorded. Emission spectra were recorded on a ISA Jobin-Yvon spex Fluoro-Max-2 apparatus and samples were analyzed during a time period of 10 hours. All of the spectra were recorded with excitation at 400 nm. Amyloid formation is detected by an increase of the emitted light and a shift of the emission maximum to a shorter wavelength (FIG. 7). The ratio of the intensity of the emitted light at 560 nm (intra-chain process) and 600 nm (inter-chain-process) can be used to detect amyloid formation of bovine insulin (FIG. 8).

Example 4

Figure 9:
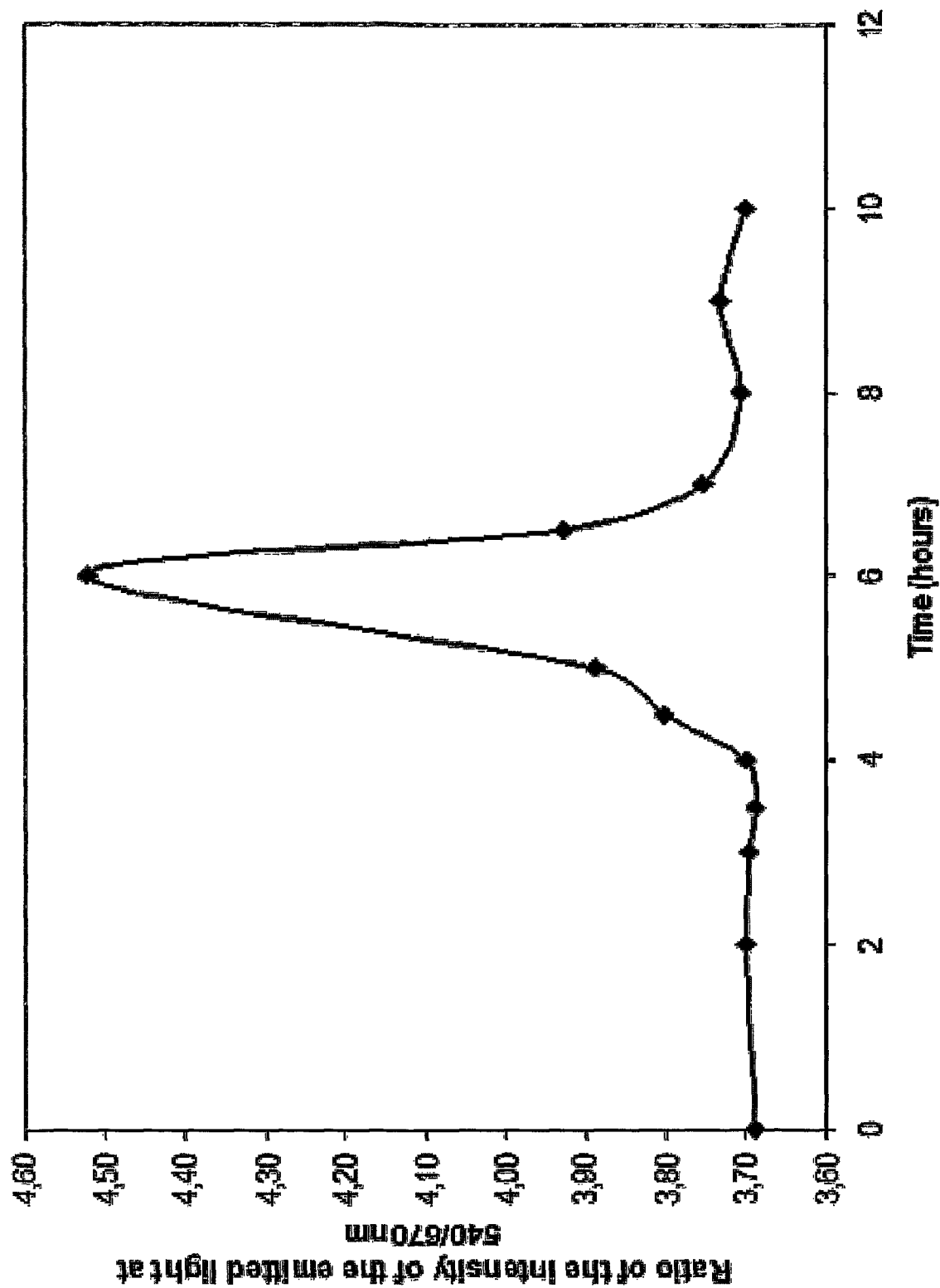
FIG. 9 shows the changes of the ratio of the intensity of the emitted light at 540 nm and 670 nm of 30 µM POWT (on a monomer basis) with an aliquot of 5 µM insulin in 20 mM Na-phosphate buffer pH 1.6, during amyloid formation in the bovine insulin (0.3 mM, pH 1.6 65° C.).

Fluorescent Detection of Amyloid Formation of Bovine Insulin in Solution, Using POWT A stock-solution containing 1.0 mg POWT/ml in deionized water was prepared. A stock solution containing 320 µM bovine insulin in 25 mM HCl was placed in a water bath (65° C.) to induce the amyloid formation. For the emission measurements 10 µl of the polymer stock-solution was mixed with 25 µl of the insulin stock-solution, and diluted to a final volume of 1500 µl with 25 mM HCl. After 5 minutes of incubation, the emission spectrum was recorded. Emission spectra were recorded on a ISA Jobin-Yvon spex Fluoro-Max-2 apparatus and samples were analyzed during a time period of 10 hours. All of the spectra were recorded with excitation at 400 nm. Amyloid formation is detected by a taking the ratio of the intensity of the emitted light at 540 nm (intra-chain process) and 670 nm (inter-chain process) (FIG. 9).

Example 5

Histological Staining of Pancreas Tissue with POMT

Figure 10:
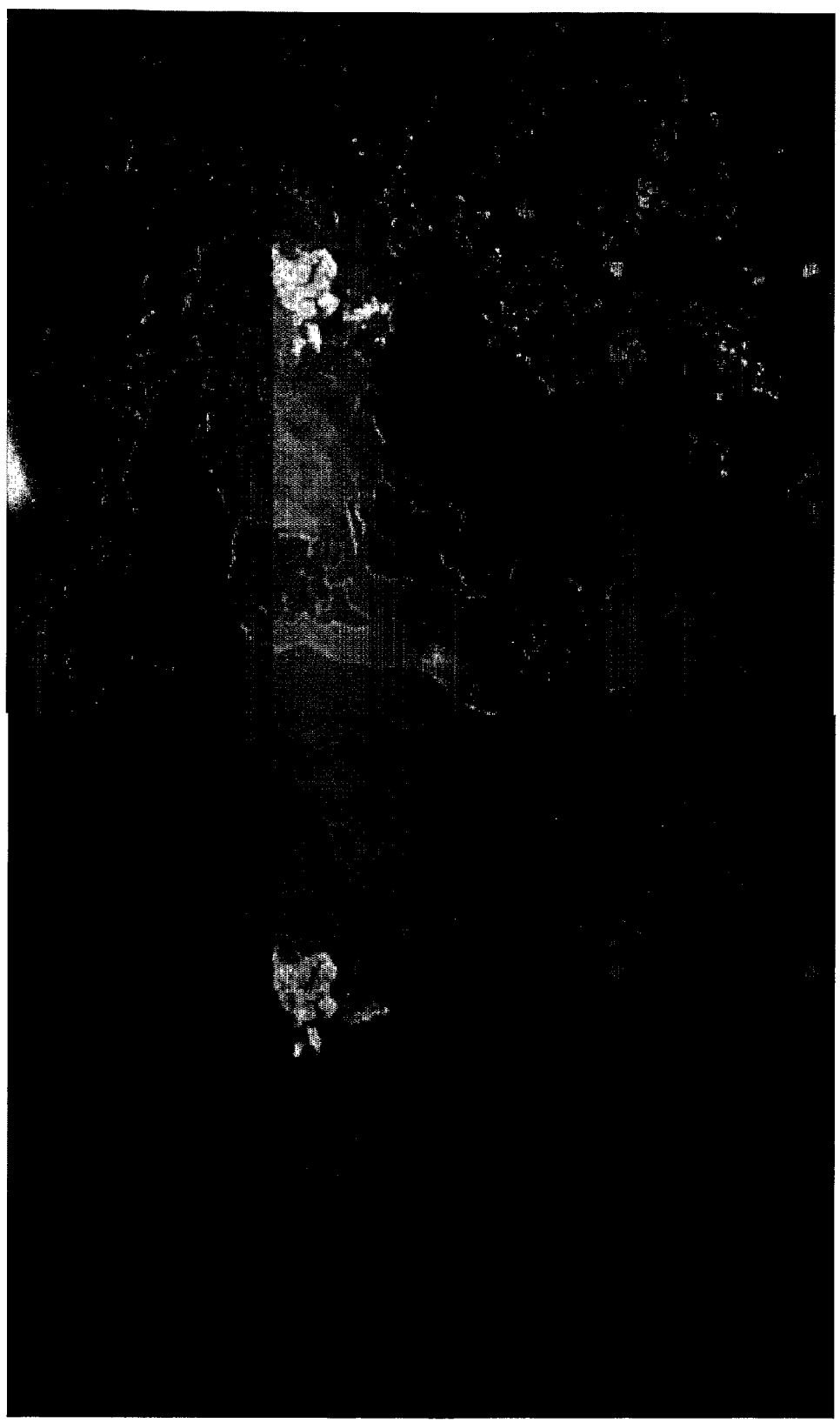
FIG. 10 shows the fluorescence images of pancreas tissue stained with POMT. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AIAPP has pink and red colour, respectively.

Frozen sections from pancreas were fixed in ice cold acetone or ethanol for 10 minutes and washed with 0.15 M TBS buffer. The sections were equilibrated in incubation buffer solution, 100 mM Na-Carbonate pH 10, for 10 min. POMT were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of POMT, due to interaction with the AIAPP (amyloid islet amyloid polypeptide), are seen as a change of the colour and the intensity of the emitted light from POMT (FIG. 10). AIAPP is associated with diseases, such as Type 2 diabetes and insulinoma. Some pancreas tissue contained large amounts of fat. This was removed by incubation in a chloroform:methanol 2:1 mixture.

Example 6

Histological Staining of Pancreas Tissue with PONT

Figure 11:
FIG. 11 shows the fluorescence images of pancreas tissue stained with PONT. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AIAPP has pink and red colour, respectively

Frozen sections from pancreas were fixed in ice cold acetone or ethanol for 10 minutes and washed with 0.15 M TBS buffer. The sections were equilibrated in incubation buffer solution, 100 mM Glycine pH 1.8, for 10 min. PONT were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PONT, due to interaction with the AIAPP (amyloid islet amyloid polypeptide), are seen as a change of the colour and the intensity of the emitted light from PONT (FIG. 11). AIAPP is associated with diseases, such as Type 2 diabetes and insulinoma. Some pancreas tissue contained large amounts of fat. This was removed by incubation in a chloroform methanol 2:1 mixture.

Example 7

Histological Staining of Pancreas Tissue with PTAA

Figure 12:
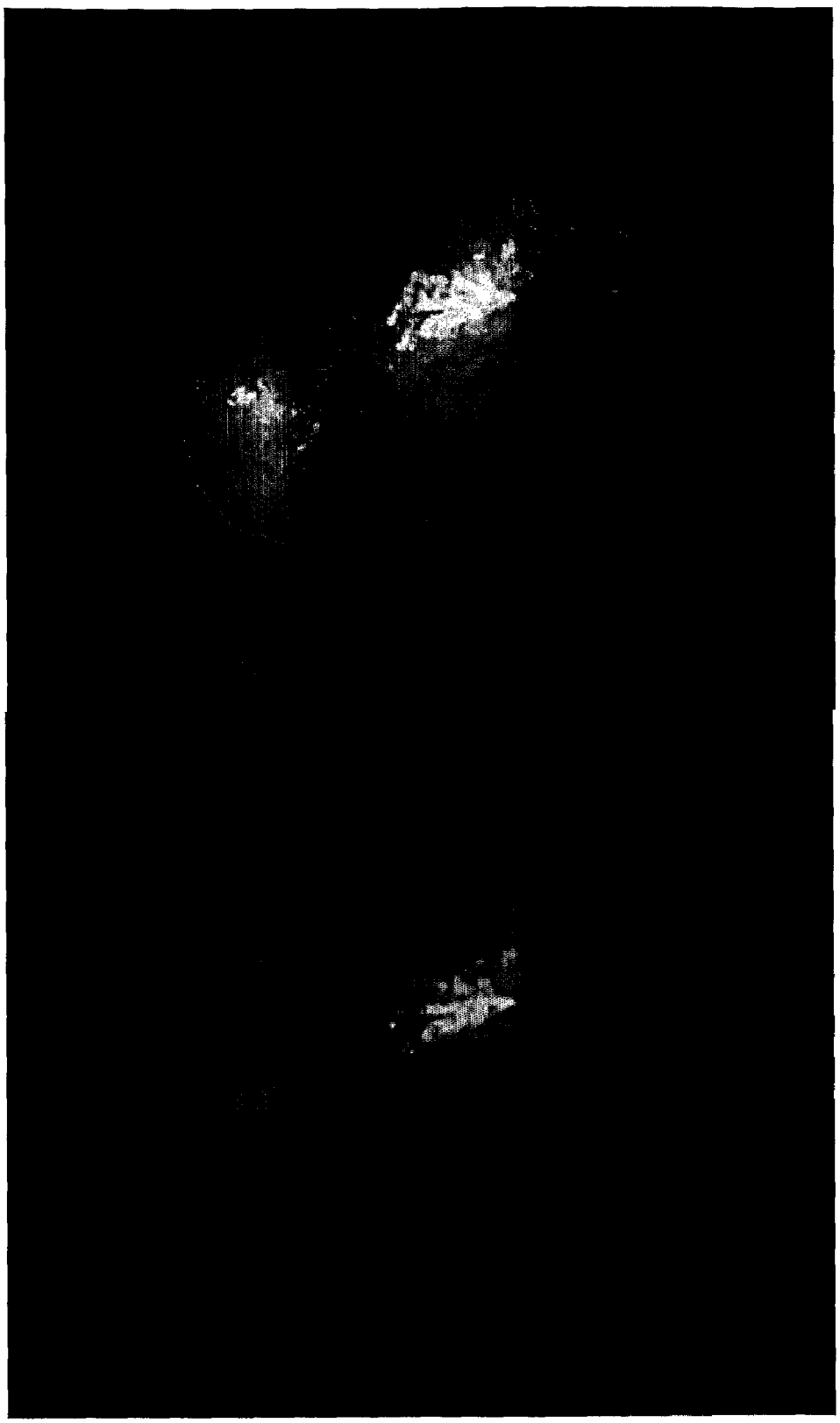
FIG. 12 shows the fluorescence images of pancreas tissue stained with PTAA. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AIAPP has pink and red colour, respectively

Frozen sections from pancreas were fixed in ice cold acetone or ethanol for 10 minutes and washed with 0.15 M TBS buffer. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AIAPP (amyloid islet amyloid polypeptide), are seen as a change of the colour and the intensity of the emitted light from PTAA (FIG. 12). AIAPP is associated with diseases, such as Type 2 diabetes and insulinoma. Some pancreas tissue contained large amounts of fat. This was removed by incubation in a chloroform methanol 2:1 mixture.

Example 8

Histological Staining of Adrenal Glands Tissue with PTAA

Figure 13:
FIG. 13 shows the fluorescence image of adrenal gland tissue stained with PTAA. The fluorescence was recorded with an epifluorescence microscope (Zeiss Axiovert inverted microscope A200 Mot) equipped with a CCD camera (Axiocam HR). Emission filter 546 nm shows the AA with red colour.

Sections (5 µm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AA (amyloid A), are seen as a change of the colour and the intensity of the emitted light from PTAA (FIG. 13). AA is associated with diseases, such as Secondary amyloidosis and familial Mediterranean fever.

Example 9

Histological Staining of Kidney Tissue with PTAA

Figure 14:
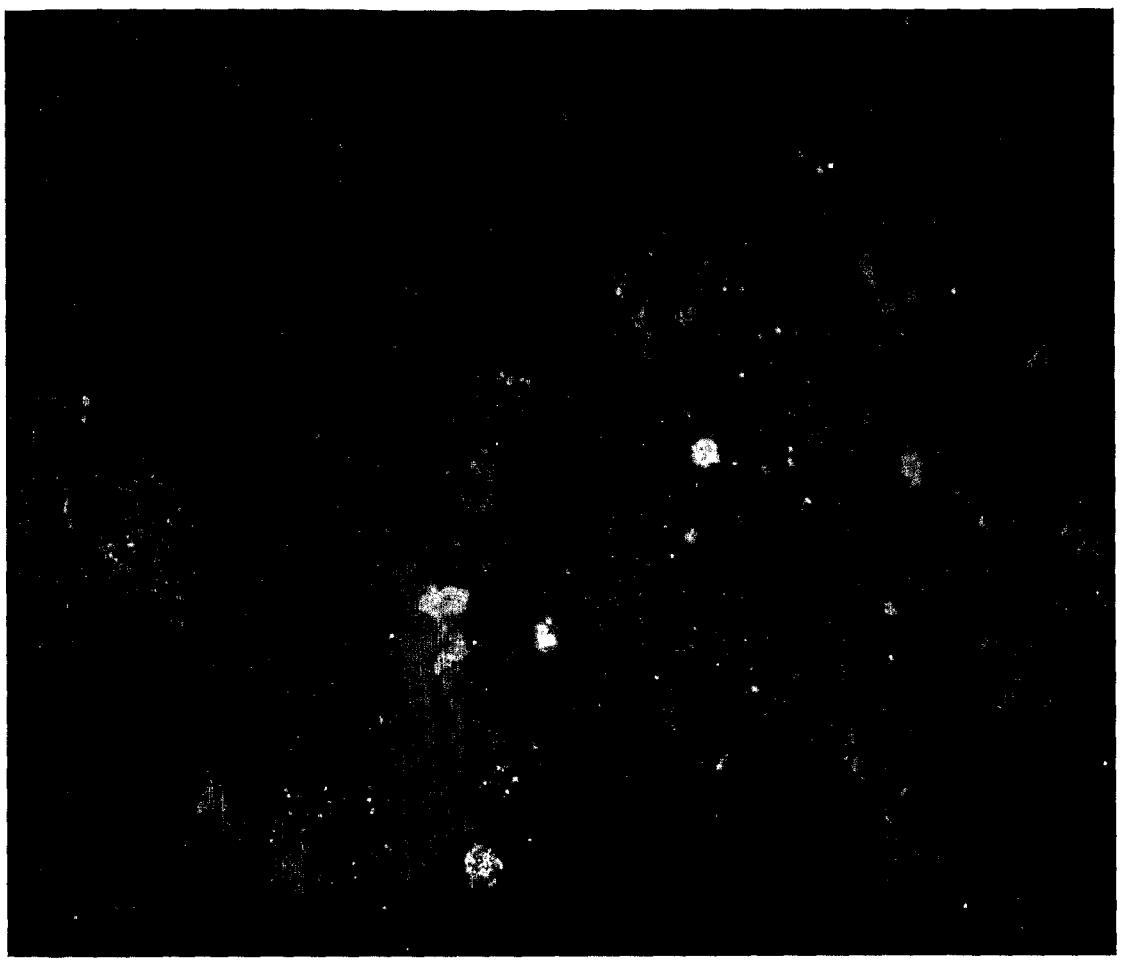
FIG. 14 shows the fluorescence image of kidney tissue stained with PTAA. The fluorescence was recorded with an epifluorescence microscope (Zeiss Axiovert inverted microscope A200 Mot) equipped with a CCD camera (Axiocam HR). Emission filter 546 nm shows the AA with red colour.

Sections (5 µm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AA (amyloid A), are seen as a change of the colour and the intensity of the emitted light from PTAA (FIG. 14). AA is associated with diseases, such as Secondary amyloidosis and familial Mediterranean fever.

Example 10

Histological Staining of Liver Tissue with PTAA

Figure 15:
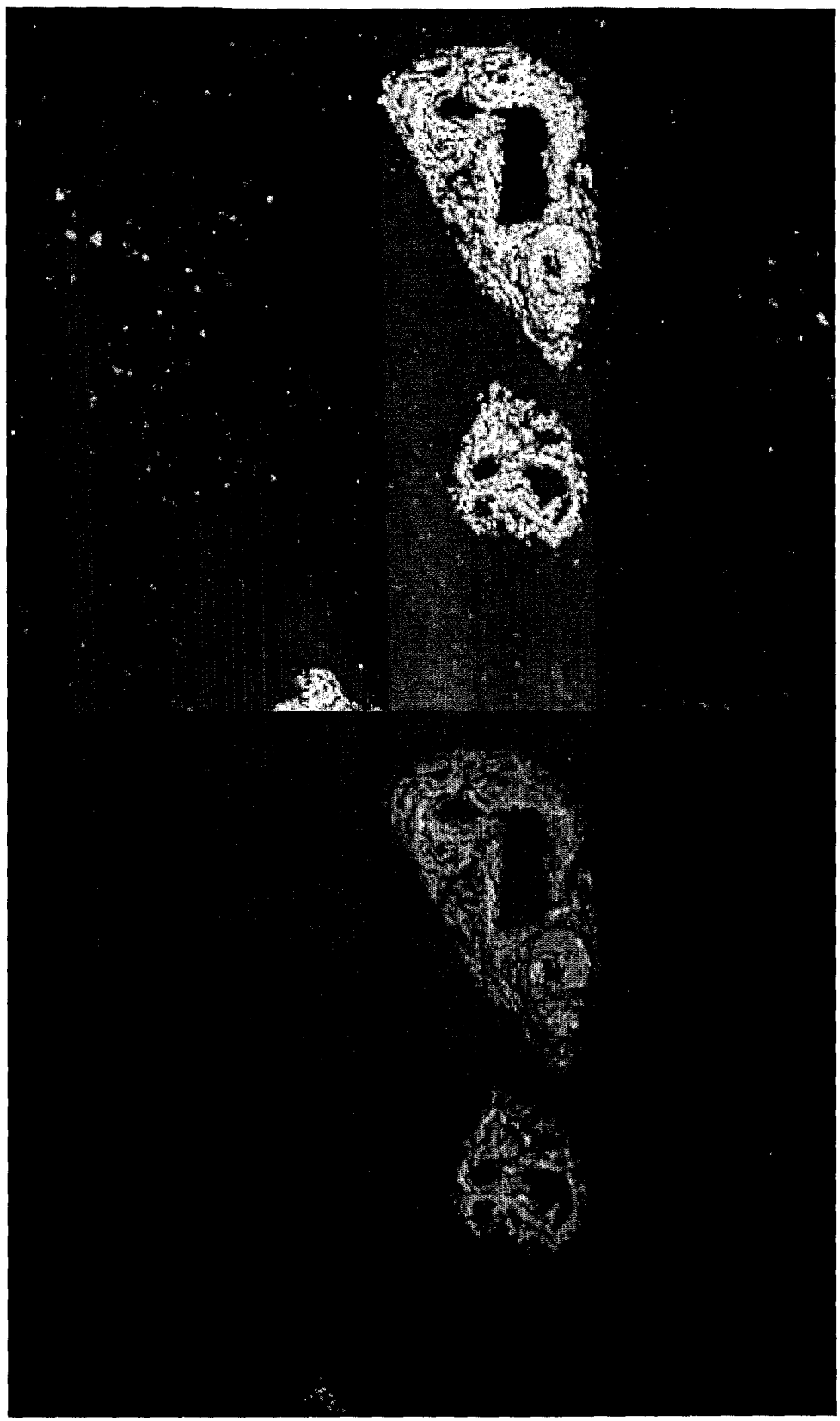
FIG. 15 shows the fluorescence images of liver tissue stained with PTAA. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AL is shown with yellow/red and red colour, respectively.

Sections (5 µm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AL (immunoglobulin light chain amyloid), are seen as a change of the colour and the intensity of the emitted light from PTAA (FIG. 15). AL is associated with disease, such as Primary AL amyloidosis, myeloma-associated or macroglobulinaemia-associated Example 11

Histological Staining of Kidney Tissue with PTAA

Figure 16:
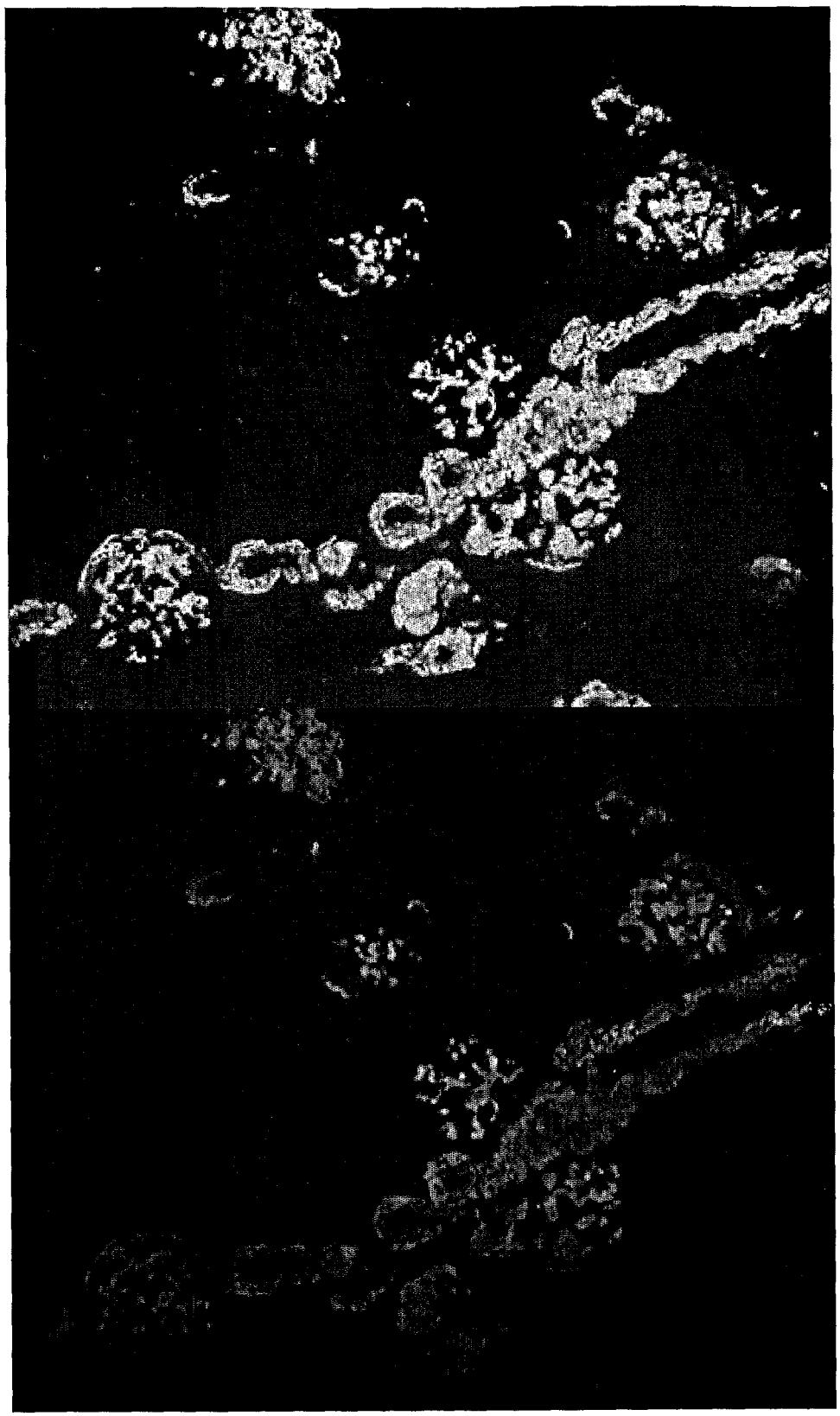
FIG. 16 shows the fluorescence images of kidney tissue stained with PTAA. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AL is shown with yellow/red and red colour, respectively.

Sections (5 µm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AL (immunoglobulin light chain amyloid), are seen as a change of the colour and the intensity of the emitted light from PTAA (FIG. 16). AL is associated with disease, such as Primary AL amyloidosis, myeloma-associated or macroglobulinaemia-associated Example 12

Histological Staining of Muscle Layer in Intestine with PTAA

Figure 17:
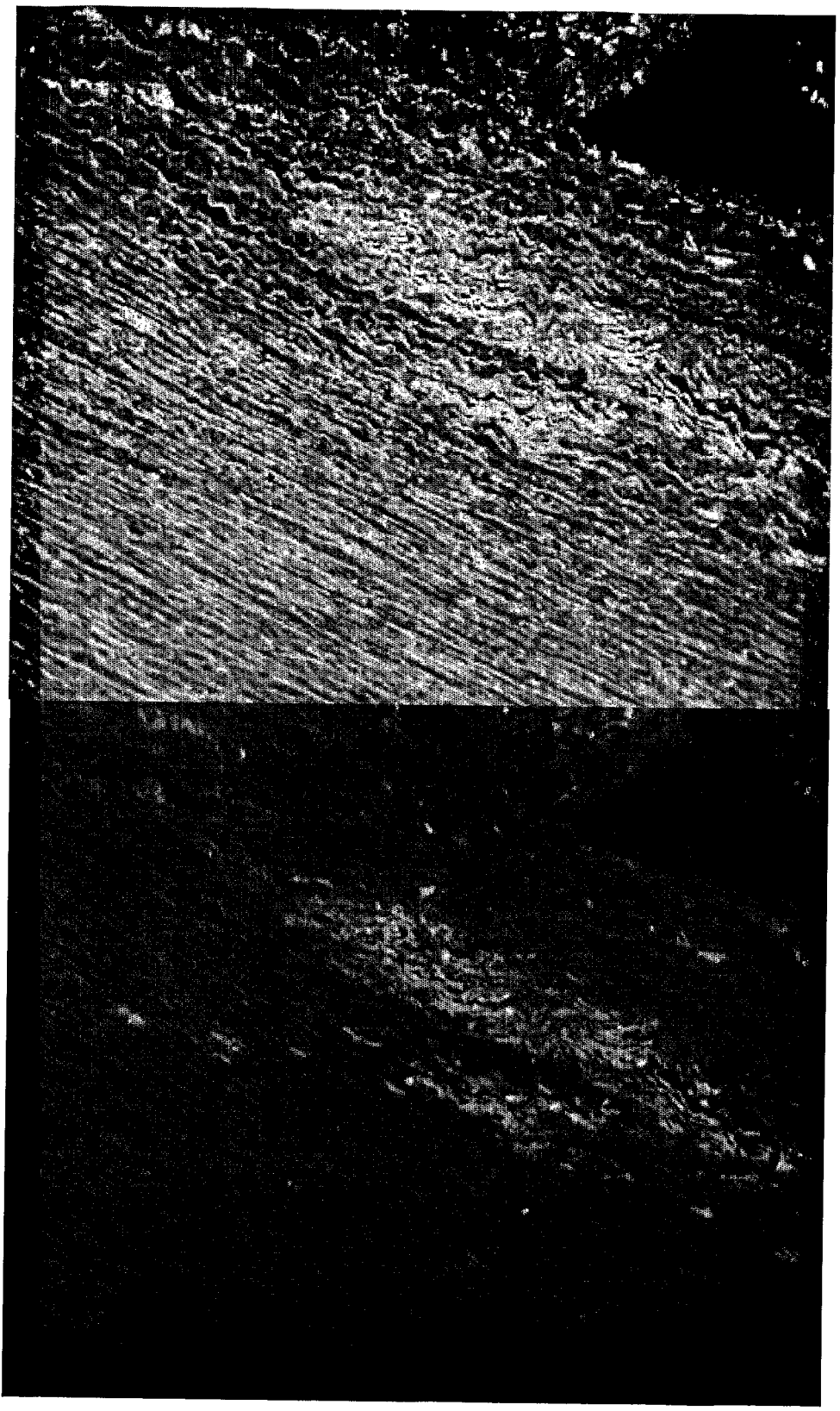
FIG. 17 shows the fluorescence images of a muscle layer in the intestine stained with PTAA. The fluorescence was recorded with an epifluorescence microscope (Zeiss Axiovert inverted microscope A200 Mot) equipped with a CCD camera (Axiocam HR). Filters 405/470/546 nm (top) and Filter 546 nm (bottom). The AL is shown with yellow and red colour, respectively.

Sections (5 µm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 µg probe in 100 µl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the AL (immunoglobulin light chain amyloid), are seen as a change of the colour and the intensity of the emitted light from PTAA (FIG. 17). AL is associated with disease, such as Primary AL amyloidosis, myeloma-associated or macroglobulinaemia-associated Example 13

Histological Staining of Brain Tissue with PTAA

Figure 18:
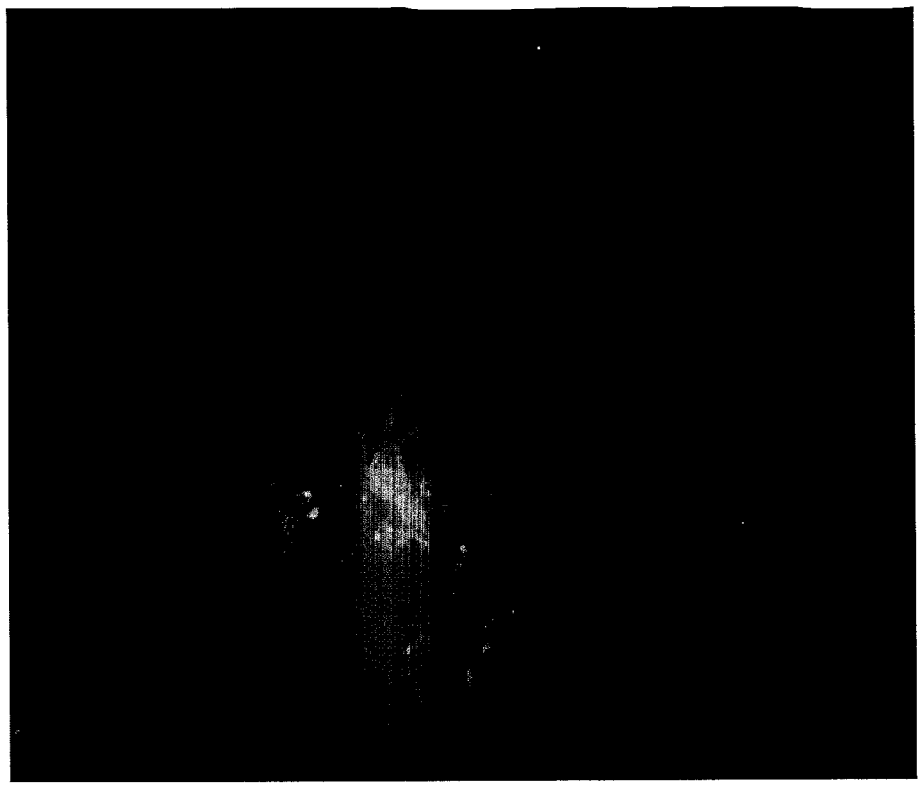
FIG. 18 shows the fluorescence image of brain tissue stained with PTAA. The fluorescence was recorded with an epifluorescence microscope (Zeiss Axiovert inverted microscope A200 Mot) equipped with a CCD camera (Axiocam HR). Emission filter 546 nm shows the A-beta plaque with red colour.

Sections (5 μm) from formaldehyde-fixed, paraffin-embedded amyloid-containing tissue were placed on plus-slides (Histolab, Gothenburg, Sweden) and deparaffinized with xylene (2×30 min), absolute alcohol (2×10 min), 95% alcohol (10 min) and 70% alcohol (10 min) and finally rinsed in distilled water for a couple of minutes. The sections were equilibrated in incubation buffer solution, 100 mM Na-Carbonate pH 10, for 10 min. PTAA were mixed with the same buffer used for equilibration (0.25 μg probe in 100 μl) and added to the sections. The incubation took place in a humidity chamber for 2 hours and superfluous probe solution was washed away with incubation buffer. The fluorescence from the tissues samples were recorded with an epifluorescence microscope (Zeiss Axiovert inverted microscope A200 Mot) equipped with a CCD camera (Axiocam HR), using a 405/30 nm bandpass filter (LP450), a 470/40 nm bandpass filter (LP515) and a 546/12 nm bandpass filter (LP590). The alterations of the intra- and interchain processes of PTAA, due to interaction with the A-beta plaque, are seen as a change of the colour and the intensity of the emitted light from PTAA (FIG. 18). A-beta plaque is associated with disease, such as Alzheimer's disease.

Example 14

Staining of Mixture of Collagen and Amyloid Insulin Fibrils with PONT

Figure 19:
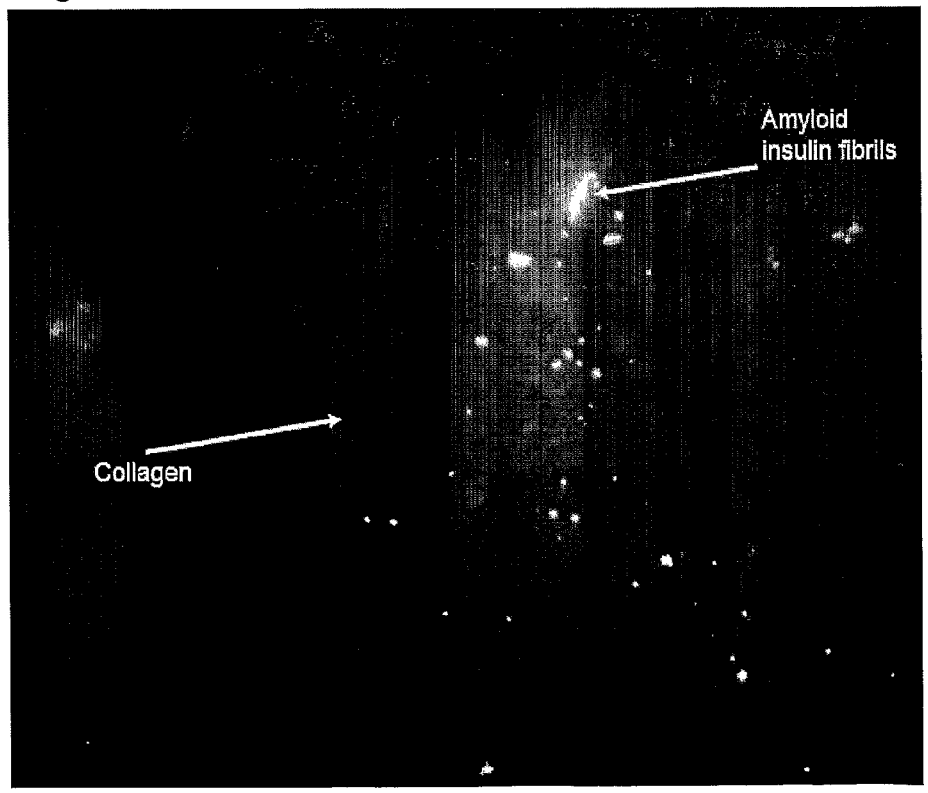
FIG. 19 shows a fluorescence image of a mixture of collagen and amyloid insulin fibrils stained with PONT. The fluorescence was recorded with an epifluorescence microscope (Zeiss Axiovert inverted microscope A200 Mot) equipped with a CCD camera (Axiocam HR). Emission filter 470 nm shows collagen/PONT with red colour and amyloid insulin fibrils/PONT with yellow/green colour. The difference in the colour emitted from PONT is due to differences in the intrinsic conformation, helical and β-sheet, of the two proteins.

Collagen type I (from white rabbit skin; Sigma) was dissolved in 0.5 M HAc to a final concentration of 320 μM. 20 μl of this solution was mixed with 2 μl of the fBI solution (320 μM) and diluted to a final volume of 100 μl with deionized water. A droplet, 2 μl, of the mixture was placed on a microscope slide and after drying, the spot was stained with a droplet (1 μl) of the PONT solution (1.0 mg ml$^{-1}$) for 1 minute. The excess of unbound PONT was removed by extensive rinsing in de-ionized water. The fluorescence from the PONT/protein complexes on the microscope slide were recorded with an epifluorescence microscope (Zeiss Axiovert inverted microscope A200 Mot) equipped with a CCD camera (Axiocam HR), using a 405/30 nm filter (LP450, exposure time: 1500 ms). The difference in color between the PONT/collagen complex and the PONT/Amyloid insulin fibril complex are shown in FIG. 19. Collagen is a fibrous protein with macromolecular helical structure and intrinsic helical structure, and the interaction with PONT will force the polyelectrolyte chains to adopt a geometry that emits red light. Amyloid insulin fibrils also have macromolecular helical structure but the fibrils has intrinsic β-sheet structure and the interaction with PONT will force the polyelectrolyte chains to adopt a geometry that emits green/yellow light. The difference in the color emitted from PONT is due to differences in the intrinsic conformation, helical and β-sheet, of the two proteins.

Example 15

Microcontact Printing of POWT

Sylgard 184 (Dow Corning, UK), a two component silicone rubber (poly (dimethylsiloxane), PDMS), was used for preparing elastomer stamps used for transferring POWT to solid surfaces. The prepolymer and the curing agent is mixed according to the instructions provided by the manufacturer. This is then poured on templates prepared by photolithography using the negative [PHOTORESIST SU-8 (MICRO CHEM INC., NEWTON, Mass., USA) AS THE STRUCTURAL ELEMENT] on top of silicon wafers. Curing is accomplished by heating to [130° C.] for at least 20 min. The height of structures was 18 micrometer, and the substrate was a Si wafer cleaned in a boiling aqueous solution containing 5% each of ammonia and [H202] (TL-1 wash). The geometry for templates was designed in CleWin Version 2.51 (WieWeb Software), and transferred to a Cr mask, which was used in the photolithography step. After developing the SU-8 structures on the silicon wafer, the template, silanization (dimethyl-dicholorosilane) was done to obtain the proper surface energy of the SU-8 template. The PDMS stamps were plasma treated for ~10 sec before being dip-coated in a water-based solution of POWT (5 mg ml−1). The polymer was dried on the top of the stamp with N2. The stamp was put face down for 20-25 minutes, on a glass substrate previously cleaned with a TL-1 wash, or a polystyrene surface modified by a 10 sec oxygen plasma treatment. Both substrates were moistened before stamp contact. After removal of the stamp, POWT had partly transferred to the glass (FIG. 20).

The invention claimed is:

1. A method for detecting conformational changes and/or self-assembly/aggregation in a protein using a conjugated polyelectrolyte as a direct probe, comprising:
   i) exposing the conjugated polyelectrolyte to the protein wherein the conjugated polyelectrolyte and the protein interact directly due to non-covalent bonding;
   ii) detecting a change in at least one property of the conjugated polyelectrolyte;
   iii) using the detected change to determine the conformational changes or self-assembly/aggregation in the protein wherein the conformational changes or self-assembly/aggregation are the formation of amyloid fibrils or protofibrils.

2. The method according to claim 1, wherein said property is selected from the group consisting of fluorescence, Förster Resonance Energy Transfer (FRET), quenching of emitted light, absorption, impedance, refraction index, mass, viscoelastic properties, thickness and other physical properties.

3. The method according to claim 1, wherein the polyelectrolyte comprises copolymers or homopolymers of thiophene, pyrrole, aniline, furan, phenylene, vinylene, fluorene or their substituted forms.

4. The method according to claim 1, wherein said conjugated polyelectrolyte has one or more anionic, cationic and/or zwitterionic side chain functionalities.

5. The method according to claim 4, wherein said ionic side chain functionalities are selected from the group comprised of amino acids, amino acid derivatives, neurotransmittors, monosaccharides, nucleic acids, and combinations and chemically modified derivatives thereof.

6. The method according to claim 1, wherein the conjugated polyelectrolyte is bound to a solid support.

7. The method according to claim 6 wherein the solid support is a microtitreplate or a flow cell.

8. The method according to claim 6, wherein the conjugated polyelectrolyte is adsorbed or covalently attached to the solid support.

9. The method according to claim 6, wherein the conjugated polyelectrolyte is in solution.

10. The method according to claim 1, wherein the conjugated polyelectrolyte is entrapped in a polymer matrix.

11. The method according to claim 1, wherein the detection of the change in at least one property of the conjugated polyelectrolyte is made in aqueous solution, organic solvent, body fluid, or in a tissue sample.

12. The method according to claim 1, wherein the non-covalent bonding is at least one of hydrogen bonding, electrostatic interactions and non-polar interactions.

13. The method according to claim 1, wherein the conjugated polyelectrolyte is a pentamer.

14. The method according to claim 1, wherein the polyelectrolyte is selected from the group consisting of poly(3-[(S)-5-amino-5-carboxyl-3-oxapentyl]-2,5-thiophenylene hydrochloride, polythiophene acetic acid, poly(3-[(S)-5-amino-5-methoxycarboxyl-3-oxapentyl]-2,5-thiophenylene hydrochloride, poly((3,3"-di[(S)-5-amino-5-carbonyl-3-oxapentyl]-2,2'; 5',2"])-5,5"-terthiophenylene hydrochloride and poly((1,4-di(3-[(S)-5-amino-5-carbonyl-3-oxapentyl]-thiophen-2-yl)-benzene) hydrochloride.

* * * * *

UNITED STATES PATENT AND TRADEMARK OFFICE
CERTIFICATE OF CORRECTION

PATENT NO. : 7,867,718 B2
APPLICATION NO. : 11/579741
DATED : January 11, 2011
INVENTOR(S) : Nilsson et al.

It is certified that error appears in the above-identified patent and that said Letters Patent is hereby corrected as shown below:

In the bibliographic information at Ref. (73) after the name of Assignee, BioChromix, please delete "Linkoping" and replace it with --Solna--.

In claim 9, column 16, line 64, delete "claim 6" and replace it with --claim 1--.

Signed and Sealed this
Tenth Day of May, 2011

David J. Kappos
*Director of the United States Patent and Trademark Office*